(12) United States Patent
Cullin et al.

(10) Patent No.: US 10,607,468 B2
(45) Date of Patent: Mar. 31, 2020

(54) COMMUNICATION APPARATUS AND SYSTEM, AND METHOD

(71) Applicant: Doro AB, Malmö (SE)

(72) Inventors: Peter Cullin, Staffanstorp (SE); Jérôme Arnaud, Meudon (FR); Acher Criou, Neuilly-sur-Seine (FR); Fredrik Palmqvist, Limhamn (SE); David Kay, Malmö (SE); Xavier Corbin, Chevreuse (FR); Fredrik Jacobsson, Landskrona (SE); Peter Johansson, Flyinge (SE); Alf Ingvarsson, Sjöbo (SE)

(73) Assignee: Doro AB, Malmo (SE)

( * ) Notice: Subject to any disclaimer, the term of this patent is extended or adjusted under 35 U.S.C. 154(b) by 0 days.

(21) Appl. No.: 16/230,413

(22) Filed: Dec. 21, 2018

(65) Prior Publication Data
US 2019/0197862 A1 Jun. 27, 2019

Related U.S. Application Data

(63) Continuation of application No. 15/322,704, filed as application No. PCT/EP2015/064734 on Jun. 29, 2015, now Pat. No. 10,204,500.

(30) Foreign Application Priority Data

Jul. 2, 2014 (EP) ..................... 14290195
Feb. 27, 2015 (EP) ..................... 15156937

(51) Int. Cl.
*G08B 21/04* (2006.01)
*G08B 25/00* (2006.01)
(Continued)

(52) U.S. Cl.
CPC ......... *G08B 21/0415* (2013.01); *G06F 19/00* (2013.01); *G06F 19/3418* (2013.01);
(Continued)

(58) Field of Classification Search
CPC ............ G08B 21/0415; G08B 21/0461; G08B 21/02; G08B 25/001; G08B 25/005;
(Continued)

(56) References Cited

U.S. PATENT DOCUMENTS 6,208,251 B1 3/2001 Cadet et al.
10,169,607 B1 * 1/2019 Sheth .................. G06F 21/6245
(Continued)

FOREIGN PATENT DOCUMENTS

WO WO 2004/091107 A2 10/2004
WO WO 2007/060558 A2 5/2007
(Continued)

OTHER PUBLICATIONS

International Search Report for PCT/EP2015/064734, dated Jan. 4, 2016.
(Continued)

*Primary Examiner* — Hung T Nguyen
(74) *Attorney, Agent, or Firm* — Merchant & Gould P.C.

(57) ABSTRACT

A communication apparatus includes a controller. The controller is configured to: receive a message, such as a communication request; determine a type for said message; select a first recipient layer based on said type, said first recipient layer comprising at least one recipient; transmit said message to at least one of said at least one recipient of said first recipient layer; receive a confirmation from said at least one of said at least one recipient of said first recipient layer; and in response thereto transmit said confirmation from said at least one of said at least one recipient of said first recipient layer to at least another one of said at least one recipient of said first recipient layer.

26 Claims, 23 Drawing Sheets

(51) Int. Cl.
  *G08B 25/01* (2006.01)
  *G06F 19/00* (2018.01)
  *H04M 1/725* (2006.01)
  *G16H 80/00* (2018.01)
  *G16H 40/63* (2018.01)

(52) U.S. Cl.
  CPC ....... *G08B 21/0461* (2013.01); *G08B 25/001* (2013.01); *G08B 25/005* (2013.01); *G08B 25/006* (2013.01); *G08B 25/009* (2013.01); *G08B 25/016* (2013.01); *G16H 40/63* (2018.01); *G16H 80/00* (2018.01); *H04M 1/72541* (2013.01)

(58) Field of Classification Search
  CPC .. G08B 25/006; G08B 25/009; G08B 25/016; G08B 25/12; G16H 80/00; G16H 40/63; H04M 1/7241; H04M 1/72541; H04M 11/04; H04W 4/22; H04W 64/00; G06F 19/00; G06F 19/3418
  USPC ... 340/539.11, 539.12, 573.1, 573.3, 286.07; 455/404.1, 404.2; 702/188; 705/2, 3
  See application file for complete search history.

(56) References Cited

U.S. PATENT DOCUMENTS

| | | |
|---|---|---|
| 2001/0032244 A1 | 10/2001 | Neustel |
| 2002/0082665 A1* | 6/2002 | Haller ................ A61N 1/37264 607/60 |
| 2003/0172940 A1* | 9/2003 | Rogers ................ A61B 5/0031 128/899 |
| 2004/0205439 A1 | 10/2004 | Carmeli et al. |
| 2005/0283642 A1 | 12/2005 | Dill |
| 2010/0123587 A1 | 5/2010 | Walls |
| 2010/0330952 A1* | 12/2010 | Yeoman ............ H04M 1/72541 455/404.2 |
| 2012/0122420 A1 | 5/2012 | Franz et al. |
| 2012/0282886 A1 | 11/2012 | Amis |
| 2013/0007788 A1* | 1/2013 | Levinson ................ H04N 7/18 725/13 |
| 2013/0065569 A1 | 3/2013 | Leipzig |
| 2013/0214925 A1 | 8/2013 | Weiss |
| 2014/0039912 A1* | 2/2014 | Turinas ................ H04L 63/08 705/2 |
| 2014/0097961 A1 | 4/2014 | Vaglio et al. |
| 2015/0002293 A1 | 1/2015 | Nepo |
| 2015/0035675 A1 | 2/2015 | Gunaratnam et al. |
| 2015/0350860 A1 | 12/2015 | Wimmer et al. |

FOREIGN PATENT DOCUMENTS

| | | |
|---|---|---|
| WO | WO 2009/137590 A2 | 11/2009 |
| WO | WO 2013/077853 A1 | 5/2013 |

OTHER PUBLICATIONS

European Search Report for EP 14290195.8, dated Mar. 24, 2015.
Office Action for European Patent Application No. 14290195.8, dated Jul. 24, 2017.

* cited by examiner

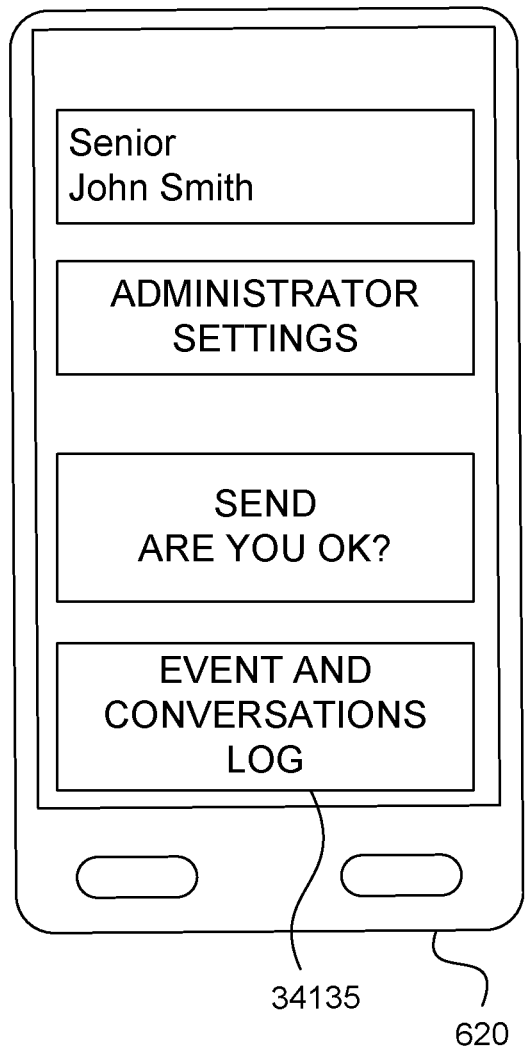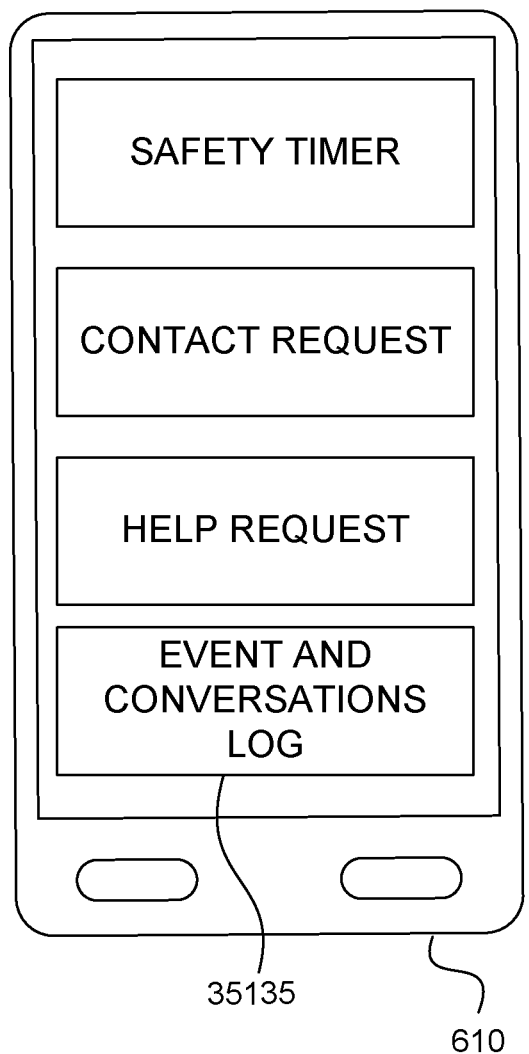
Fig. 34
Fig. 35

COMMUNICATION APPARATUS AND SYSTEM, AND METHOD

This application is a continuation of U.S. patent application Ser. No. 15/322,704, filed 28 Dec. 2016, now issued as U.S. Pat. No. 10,204,500, which is a National Stage Application of PCT/EP2015/064734, filed 29 Jun. 2015, which claims benefit of European Patent Application No. 14290195.8, filed 2 Jul. 2014 and European Patent Application No. 15156937.3, filed 27 Feb. 2015, which applications are incorporated herein by reference. To the extent appropriate, a claim of priority is made to each of the above disclosed applications.

TECHNICAL FIELD

This application generally relates to a communications apparatus, a method, a mobile communications terminal, a system and a computer-readable storage medium for improved communication, as well as a communications apparatus, a method, a mobile communications terminal, a system and a computer-readable storage medium for addressing of messages to recipients. The application particularly relates to a communication system for providing remote care taking of a first user to be cared for by a plurality of second users, and to associated mobile communication terminals.

BACKGROUND

A technically complex problem in today's society is the care taking of persons by people being related in some way to that person. A typical person to be cared for is a senior citizen who is still capable of living at his or her own home, but nevertheless needs certain care taking when feeling generally lonely, facing a task which is difficult to perform alone given his or her physical or mental capability, or being subject to an unexpected situation of emergency. From the perspective of people being related to the person to be cared for, the problem may accentuated by reasons such as large geographical distance to the person to be cared for, and busy day-to-day lives.

There is thus a need for a communication system for providing remote care taking of a first user to be cared for by a plurality of second users.

In today's society many different communications systems exist. Such communications systems may be rather advanced and comprise a vast multitude of functions and possible messages and requests to be sent. Also, there may be a plurality of receivers for the various types of messages and it may sometimes be unclear what action or function should be resolved by whom and to whom a message should be sent.

This can be confusing to many users and also difficult to overlook. It may cause a delay when sending a request if it is not readily known to whom a request should be sent and a recipient has to be searched for.

Also, if different users have clearance to or needs for different data, a plurality of requests may have to be sent if it is to be sent to different users having different clearances.

There is thus a need for a communications system wherein the selection of a recipient is simplified.

SUMMARY

It is accordingly an object of the present disclosure to eliminate, alleviate, mitigate or reduce at least some of the problems referred to above, by an improved communication system and associated mobile communication terminals.

One aspect of the present disclosure is therefore a communication system for providing remote care taking of a first user to be cared for by a plurality of second users. The system comprises a first mobile communication terminal configured for use by the first user to be cared for, and a plurality of second mobile communication terminals for use by the second users, each second mobile communication terminal being configured to let the respective second user act as a member of a first recipient layer or a member of a second recipient layer.

The first mobile communication terminal is configured to allow the first user to select a first element in a user interface of the first mobile communication terminal to cause sending of a first type of remote care taking request message intended for second users being members of the first recipient layer, the first type of request message pertaining to remote care taking of the first user.

The first mobile communication terminal is also configured to allow the first user to select a second element in the user interface of the first mobile communication terminal to cause sending of a second type of request message intended for second users being members of the second recipient layer, the second type of request message pertaining to remote care taking of the first user and being different from the first type of request message.

Another aspect of the present disclosure is a mobile communication terminal being configured to act as the first mobile communication terminal as defined above for the first aspect.

Still another aspect of the present disclosure is a mobile communication terminal being configured to act as the second mobile communication terminal as defined above for the first aspect.

Further, a related object is to eliminate, alleviate, mitigate or reduce at least some of the problems referred to above by providing a communication apparatus comprising a controller, wherein said controller is configured to receive a message, such as a communication request, determine a type for said message, select a first recipient layer based on said type, said first recipient layer comprising at least one recipient, and transmit said message to at least one of said at least one recipient of said first recipient layer.

Another related object is to eliminate, alleviate, mitigate or reduce at least some of the problems referred to above by providing a method for use in a communication apparatus, wherein said method comprises receiving a message, such as a communication request, determining a type for said message, selecting a first recipient layer based on said type, said first recipient layer comprising at least one recipient, and transmitting said message to at least one of said at least one recipient of said first recipient layer.

In a related embodiment, the first recipient layer is selected among a set of layers comprising at least said first recipient layer, a second recipient layer as well as a third recipient layer. Moreover, in this advantageous embodiment, the message is transmitted to all recipients of the selected layer. Having at least three recipient layers which are selectable based on message type and for which the message will be transmitted to all respective recipients in the selected layer, will offer a flexible and efficient message handling scheme.

In this or another related embodiment, the controller of the communication apparatus is further configured to receive a confirmation from one or more of the recipients of said first recipient layer to which the message has been transmitted, and in response thereto transmit the confirmation to at least another one of the recipients of the first recipient layer, preferably to all of the other recipients of the first recipient layer. This will further improve the flexibility and efficiency of the message handling scheme.

A related object of the teachings of this application is to eliminate, alleviate, mitigate or reduce at least some of the problems referred to above by providing a mobile communications terminal being associated with a first recipient layer and comprising a controller, wherein said controller is configured to receive a message, such as a communication request, wherein said message is associated with said first recipient layer.

A related an object of the teachings of this application is to eliminate, alleviate, mitigate or reduce at least some of the problems referred to above by providing a mobile communications terminal comprising a controller, wherein said controller is configured to generate a message, such as a communication request, and associate said message with a type.

A related object of the teachings of this application is to eliminate, alleviate, mitigate or reduce at least some of the problems referred to above by providing a communications system comprising a communication apparatus and a first mobile communication terminal and a second mobile communication terminal, wherein said first mobile communication terminal possibly comprises said communication apparatus and wherein said first mobile communication terminal is configured to generate a message, such as a communication request, and associate said message with a type, wherein said communication apparatus is configured to receive a message, such as a communication request, determine a type for said message, select a first recipient layer based on said type, and transmit said message to at least said second mobile communication terminal, and wherein said second mobile communication terminal is associated with said first recipient layer and configured to receive said message.

A related object of the teachings of this application is to eliminate, alleviate, mitigate or reduce at least some of the problems referred to above by providing a method for use in a communications system comprising a communication apparatus, a first mobile communication terminal and a second mobile communication terminal, wherein said first mobile communication terminal possibly comprises said communication apparatus and wherein said method comprises generating a message, such as a communication request, and associating said message with a type, receiving said message and determining a type for said message, selecting a first recipient layer based on said type, transmitting said message to at least said second mobile communication terminal, and receiving said message.

The method mentioned immediately above may further comprise: generating a message in said second mobile communication terminal, said message being associated with an are you ok type (ARE YOU OK); transmitting said message to said first mobile communication terminal belonging to a person cared for; determining that no response to said message is received; and, in response thereto, generating and transmitting an alarm request.

Moreover, this method may further comprise: selecting a forwarding recipient layer; and transmitting said received message to at least one of at least one recipient of said forwarding recipient layer.

It is also a related object of the teachings of this application to eliminate, alleviate, mitigate or reduce at least some of the problems referred to above by providing a computer program product possibly stored on a computer-readable medium for implementing any of the methods according to the above.

It is further a related object of the teachings of this application to eliminate, alleviate, mitigate or reduce at least some of the problems referred to above by providing a computer-readable storage medium encoded with instructions that, when executed on a processor, perform any of the methods according to above.

One insight of the present disclosure is that by arranging recipients in layers and associating each recipient layer with a message type, a message may be directed to an appropriate recipient without the sender having to know or worry about who he is sending the message to.

The teachings herein may find use in telecare systems but also in other communications systems.

Other features and advantages of disclosed embodiments will appear from the following detailed disclosure, from the attached dependent claims as well as from the drawings.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise. The steps of any method disclosed herein do not have to be performed in the exact order disclosed, unless explicitly stated.

BRIEF DESCRIPTION OF DRAWINGS

The teachings herein will be described in further detail under reference to the accompanying drawings in which:

FIG. 34 shows an overview of a mobile communication terminal according to one embodiment of the teachings herein.

FIG. 35 shows an overview of a mobile communication terminal according to one embodiment of the teachings herein.

DETAILED DESCRIPTION

The disclosed embodiments will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout.

While FIGS. 36-40 disclose particularly advantageous embodiments of the subject matter of the attached independent claims, reference is first made to FIGS. 1-35 which will provide useful additional information for fully understanding these particularly advantageous embodiments.

Figure 1:
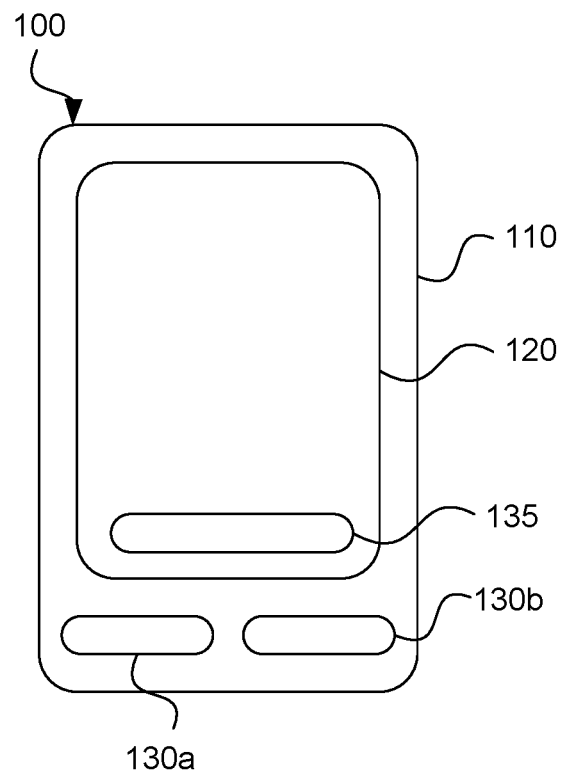
FIG. 1 shows a schematic view of a mobile communications terminal according to one embodiment of the teachings of this application.

FIG. 1 shows a schematic overview of a mobile communications terminal 100 adapted according to the teachings herein. In the embodiment shown the mobile communications terminal is a mobile phone 100. In other embodiments the mobile communications terminal 100 is computer tablet, a laptop computer, a personal digital assistant, a media player, a location finding device or any hand-held device capable of communicating with other devices. The mobile phone 100 comprises a housing 110 in which a display 120 is arranged. In one embodiment the display 120 is a touch display. In other embodiments the display 120 is a non-touch display. Furthermore, the mobile phone 100 comprises two keys 130a, 130b. In this embodiment there are two keys 130, but any number of keys, including none, is possible and depends on the design of the mobile phone 100. In one embodiment the mobile phone 100 is configured to display and operate a virtual key 135 on the touch display 120. It should be noted that the number of virtual keys 135 are dependent on the design of the mobile phone 100 and an application that is executed on the mobile phone 100. In one embodiment the communications terminal 100 comprises an ITU-T keypad or a QWERTY (or equivalent) keypad in addition to or as an alternative to a touch-sensitive display. In an embodiment where the keypad is an alternative to a touch-sensitive display, the display 120 is a non-touch-sensitive display.

Figure 2:
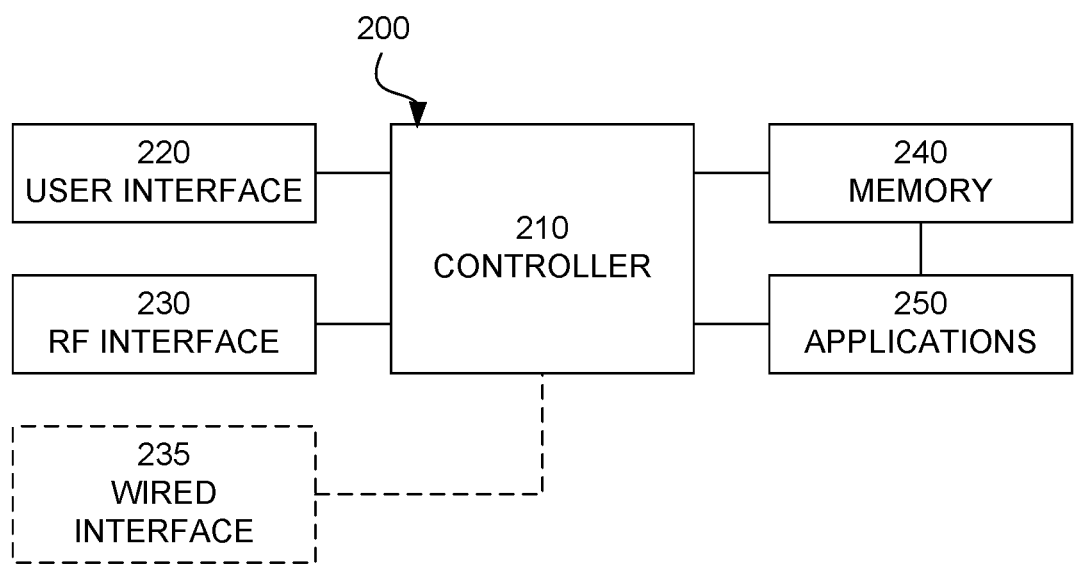
FIG. 2 shows a schematic view of the general structure of a mobile communications terminal according to one embodiment of the teachings of this application.

FIG. 2 shows a schematic view of the general structure of a mobile communications terminal 200 (100) according to FIG. 1. The mobile communications terminal 200 comprises a controller 210 which is responsible for the overall operation of the mobile communications terminal 200 and is preferably implemented by any commercially available CPU ("Central Processing Unit"), DSP ("Digital Signal Processor") or any other electronic programmable logic device. The controller 210 is implemented using instructions that enable hardware functionality, for example, by using computer program instructions executable in a general-purpose or special-purpose processor that may be stored on a computer readable storage medium (disk, memory etc) 240 to be executed by such a processor. The controller 210 is configured to read instructions from the memory 240 and execute these instructions to control the operation of the mobile communications terminal 100. The memory 240 may be implemented using any commonly known technology for computer-readable memories such as ROM, RAM, SRAM, DRAM, CMOS, FLASH, DDR, EEPROM memory, flash memory, hard drive, optical storage or any combination thereof. The memory 240 is used for various purposes by the controller 210, one of them being for storing application data and various software modules in the mobile terminal. The software modules include a real-time operating system, an application handler as well as various applications 250. The applications 250 are sets of instructions that when executed by the controller 210 control the operation of the mobile communications terminal 100. The applications 250 can include a messaging application for short messaging service (SMS), multimedia messaging service (MMS) and electronic mail, a media player application, as well as various other applications 250, such as applications for voice calling, video calling, web browsing, document reading and/or document editing, an instant messaging application, a phonebook application, a calendar application, a control panel application, one or more video games, a notepad application, location finding applications, etc. A message handler may be implemented and stored in the memory 240 as an application 250 for handling messages sent from and received at the mobile communication terminal 200.

The mobile communications terminal 200 further comprises drivers for a user interface 220, which in the mobile communications terminal 100 of FIG. 1 is comprised of the display 120, the keys 130, 135, a microphone and a loudspeaker. The user interface (UI) drivers 220 also includes one or more hardware controllers, which together with the UI drivers cooperate with the display 120, keypad 130, as well as various other I/O devices such as microphone, loudspeaker, vibrator, ringtone generator, LED indicator, etc. As is commonly known, the user may operate the mobile terminal through the man-machine interface thus formed.

The mobile communications terminal 200 further comprises a radio frequency interface 230, which is adapted to allow the mobile communications terminal to communicate with other communication terminals in a radio frequency band through the use of different radio frequency technologies. Examples of such technologies are W-CDMA, GSM, UTRAN, LTE and NMT to name a few. The controller 210 is configured to operably execute the applications 250, such as the voice call and message handling applications, through the RF interface 230 and software stored in the memory 240, which software includes various modules, protocol stacks, drivers, etc. to provide communication services (such as transport, network and connectivity) for the RF interface 230, and optionally a Bluetooth interface and/or an IrDA interface for local connectivity. The RF interface 230 comprises an internal or external antenna as well as appropriate radio circuitry for establishing and maintaining a wireless link to a base station. As is well known to a person skilled in the art, the radio circuitry comprises a series of analogue and digital electronic components, together forming a radio receiver and transmitter. These components include, i.e., band pass filters, amplifiers, mixers, local oscillators, low pass filters, AD/DA converters, etc.

In one embodiment the mobile communications terminal 200 further comprises a wired interface 235 (indicated with a dashed line in FIG. 2 as this is an optional feature), which is adapted to allow the terminal to communicate with other devices through the use of different network technologies. Examples of such technologies are USB (Universal Serial Bus), Ethernet, Local Area Network, and TCP/IP (Transport Control Protocol/Internet Protocol) to name a few.

The RF interface 230 and the wired interface 235 are examples of device communication interfaces that enable communication between the mobile communications terminal 200 and another device.

Figure 3:
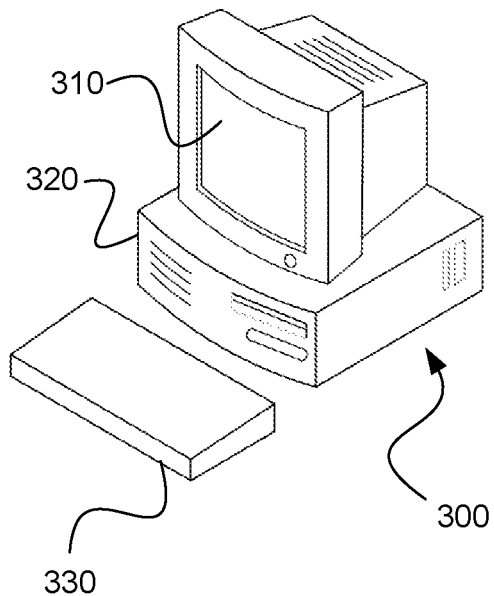
FIG. 3 is a schematic view of a server according to the teachings herein.

FIG. 3 shows a server 300 according to an embodiment herein. In one embodiment the server 300 is configured for network communication, either wireless or wired. In one embodiment the server 300 is configured for network communication, both wireless and wired. Examples of such a server 300 are: a personal computer, desktop or laptop computer, an Internet tablet computer, a mobile telephone, a smart phone, a personal digital assistant and a work station.

The server 300 will hereafter be exemplified and described as being a computer 300. The computer or terminal 300 comprises a housing 320 and may comprise a display 310. The housing comprises a controller or CPU (not shown) and one or more computer-readable storage mediums (not shown), such as storage units and internal memory. Examples of storage units are disk drives or hard drives. The server 300 further comprises at least one data port. Data ports can be wired and/or wireless. Examples of data ports are USB (Universal Serial Bus) ports, Ethernet ports or Wi-Fi (according to IEEE standard 802.11) ports. Data ports are configured to enable a terminal 300 to connect with other terminals or servers.

The terminal 300 may further comprise at least one input unit such as a keyboard 330. Other examples of input units are computer mouse, touch pads, touch screens or joysticks to name a few.

In one embodiment the server 300 is a network server. In an alternative embodiment the server 300 is implemented as a software module (250) to be executed by the mobile communication terminal 100, 200 of FIGS. 1 and 2. A message handler may be implemented as part of the software module for handling messages sent from and received at the mobile communication terminal 200.

As the message handler may be implemented centrally in a server, that in turn may be implemented in a mobile communication terminal or a server, or locally in a mobile communication terminal, it will be understood herein that the message handler is implemented in a communication apparatus that in turn may be implemented in a mobile communication terminal, as a server module in a mobile communication terminal, in a server, such as a computer, or a combination thereof.

Figure 4:
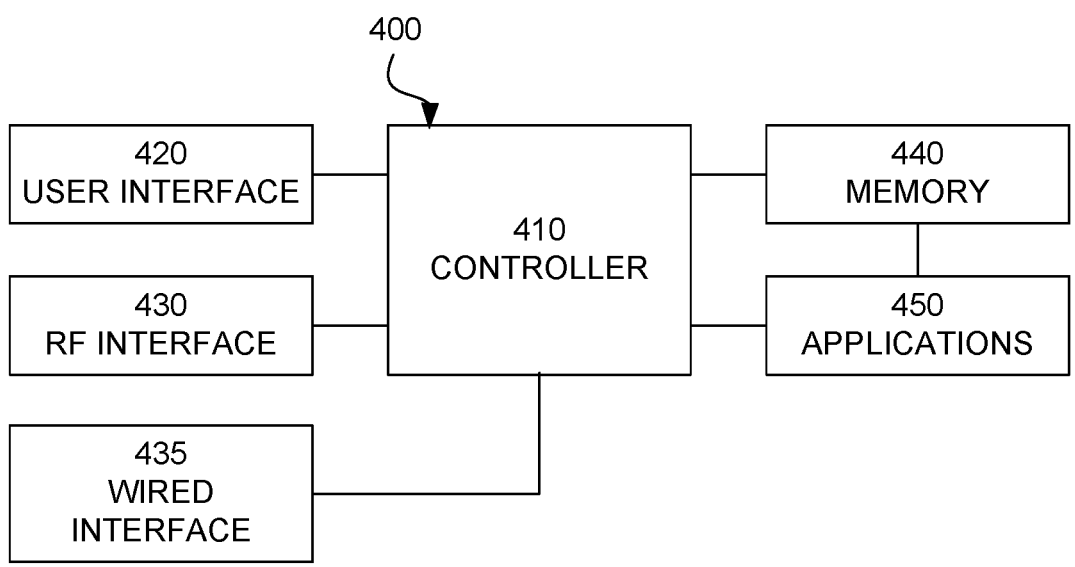
FIG. 4 is a schematic view of the components of a server according to the teachings herein.

FIG. 4 shows a schematic view of the general structure of a server 400 (300) according to FIG. 3. The server is a computer terminal 400 in one embodiment. A computer terminal 400 can be used as a server or a client and also both as a server and a client as would be appreciated by a skilled person. With reference to FIG. 4 the server will be described as being a personal computer or terminal 400, but it should be noted that a server may have the same or similar components. Typically for a server only one user interface is provided for an arrangement of computers or servers. The terminal 400 comprises a controller 410 which is responsible for the overall operation of the terminal 400 and is implemented by any commercially available CPU ("Central Processing Unit"), DSP ("Digital Signal Processor") or any other electronic programmable logic device. The controller 410 is implemented using instructions that enable hardware functionality, for example, by using executable computer program instructions in a general-purpose or special-purpose processor that may be stored on a computer readable storage medium (disk, memory etc) 440 to be executed by such a processor. The controller 410 is configured to read instructions from the memory 440 and execute these instructions to control the operation of the terminal 400. The memory 440 is implemented using any commonly known technology for computer-readable memories such as ROM, RAM, SRAM, DRAM, CMOS, FLASH, DDR, EEPROM memory, flash memory, hard drive, optical storage or any combination thereof. The terminal 400 further comprises one or more applications 450. The applications are sets of instructions that when executed by the controller 410 control the operation of the terminal 400. The memory 440 is used for various purposes by the controller 410, one of them being for storing application data and program instructions 450 for various software modules in the terminal 400. The software modules include a real-time operating system, drivers for a man-machine interface 420, an application handler as well as various applications 450. The applications 450 can include a messaging application such as electronic mail, a browsing application, a media player application, as well as various other applications 450, such as applications for voice calling, video calling, document reading and/or document editing, an instant messaging application, a calendar application, a control panel application, one or more video games, a notepad application, etc.

A message handler may be implemented and stored in the memory 440 as an application 450 for handling messages sent from and received at the mobile communication terminal 200.

The terminal 400 may further comprise drivers for a user interface 420 which in the terminal 300 of FIG. 3, is comprised of the display 310 and the keypad 330. The user interface (UI) drivers 420 also includes one or more hardware controllers, which together with the UI drivers cooperate with the display 310, keypad 330, as well as various other I/O devices such as sound system, LED indicator, etc. As is commonly known, the user may operate the terminal 400 through the man-machine interface thus formed.

The terminal 400 further comprises a radio frequency interface 430, which is adapted to allow the terminal to communicate with other devices through a radio frequency band through the use of different radio frequency technologies. Examples of such technologies are WIFI, Bluetooth®, W-CDMA, GSM, UTRAN, LTE, and NMT to name a few.

The terminal 400 further comprises a wired interface 435, which is adapted to allow the terminal to communicate with other devices through the use of different network technologies. Examples of such technologies are USB, Ethernet, and Local Area Network, TCP/IP (Transport Control Protocol/Internet Protocol) to name a few.

The controller 410 is configured to operably execute applications 450 such as the web browsing or email application through the RF interface 430 and/or the wired interface 435 using software stored in the memory 440 which software includes various modules, protocol stacks, drivers, etc. to provide communication services (such as transport, network and connectivity) for the RF interface 430 and the wired interface 435, and optionally a Bluetooth interface and/or an IrDA interface for local connectivity. The RF interface 430 comprises an internal or external antenna as well as appropriate radio circuitry for establishing and maintaining a wireless link to a base station. As is well known to a person skilled in the art, the radio circuitry comprises a series of analogue and digital electronic components, together forming a radio receiver and transmitter. These components include, i.e., band pass filters, amplifiers, mixers, local oscillators, low pass filters, AD/DA converters, etc. The RF interface 430, the wired interface 435, the Bluetooth interface and the IrDA interface are examples of device communication interfaces that enable communication between the terminal 400 and another device.

Figure 5:
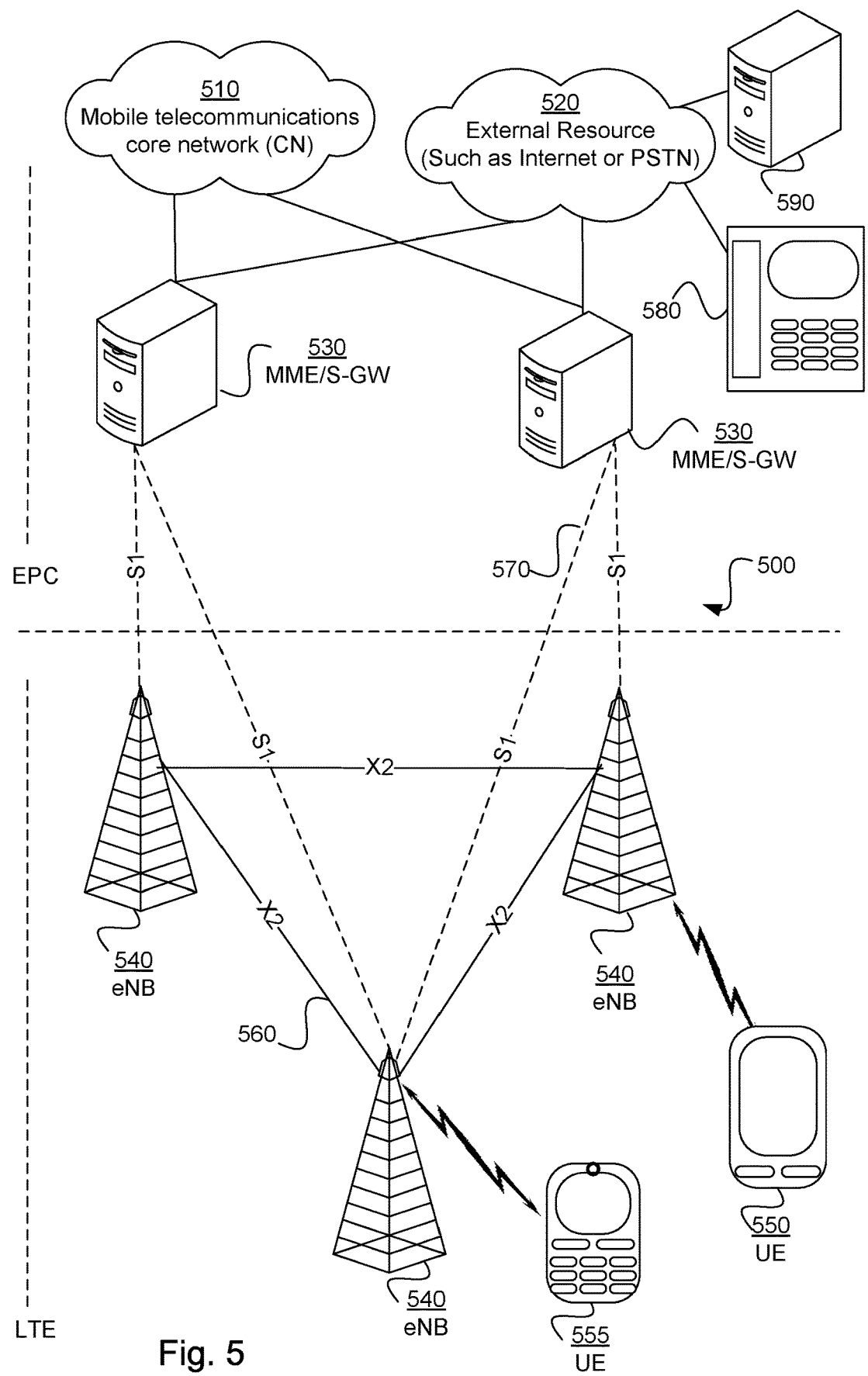
FIG. 5 show a schematic view of a telecommunications network according to one embodiment of the teachings of this application.

FIG. 5 shows a schematic view of the general structure of a telecommunications system 500 according to the teachings herein. In the telecommunication system of FIG. 5, various telecommunications services such as cellular voice calls, www/wap browsing, cellular video calls, data calls, facsimile transmissions, music transmissions, still image transmissions, video transmissions, electronic message transmissions and electronic commerce may be performed between a mobile terminal 100, 300, 550 according to the disclosed embodiments and other communications terminals, such as another mobile terminal 555 or a stationary telephone 580. The mobile terminals 550, 555 are connected to a mobile telecommunications network 510 through Radio Frequency links via base stations 540.

The telecommunications system 500 comprises at least one server 530. A server 530 has a data storage and a controller that is implemented by any commercially available CPU ("Central Processing Unit"), DSP ("Digital Signal Processor") or any other electronic programmable logic device. In one embodiment such a server is a Mobility Management Entity (MME). In one embodiment such a server is a Gateway (GW). The servers 530 are configured to communicate with a mobile telecommunications core network (CN) 510 and/or an external resource 520 such as the internet or a Public Switched Telephone Network (PSTN). A PSTN 520 is configured to communicate with and establish communication between stationary or portable telephones 580. In one embodiment the external resource comprises or is configured to communicate with an external service provider 590. In one embodiment the servers 530 are configured to communicate with other communications terminals using a packet switched technology or protocol. In such an embodiment the servers 530 may make up an Evolved Packet Core (EPC) layer.

The servers 530 are configured to communicate with nodes, also referred to as base stations 540. In one embodiment the base station 540 is an evolved Node Base (eNB). A base station 540 is further configured to communicate with a server 530. In one embodiment the communication between a server 530 and a base station 540 is effected through a standard or protocol 570. In one embodiment the protocol is S1. A base station 540 is configured to communicate with another base station 540. In one embodiment the communication between a base station 540 and another base station 540 is effected through a standard or protocol 560. In one embodiment the protocol 560 is X2. A base station 540 is further configured to handle or service a cell 580. In one embodiment the at least one base stations 540 make up a Long Term Evolution (LTE) layer. In one embodiment the at least one base stations 540 make up an LTE Advanced layer.

In one embodiment the base station 540 is configured to communicate with a mobile communications terminal 550 (100, 300) through a wireless radio frequency protocol.

In one embodiment the telecommunications system 500 is an Evolved Packet System (EPS) network. In one embodiment the telecommunications system is a system based on the 3GPP (3$^{rd}$ Generation Partnership Project) standard. In one embodiment the telecommunications system is a system based on the UMTS (Universal Mobile Telecommunications System) standard. In one embodiment the telecommunications system is a system based on a telecommunications standard such as GSM, D-AMPS, CDMA2000, FOMA or TD-SCDMA.

Figure 6:
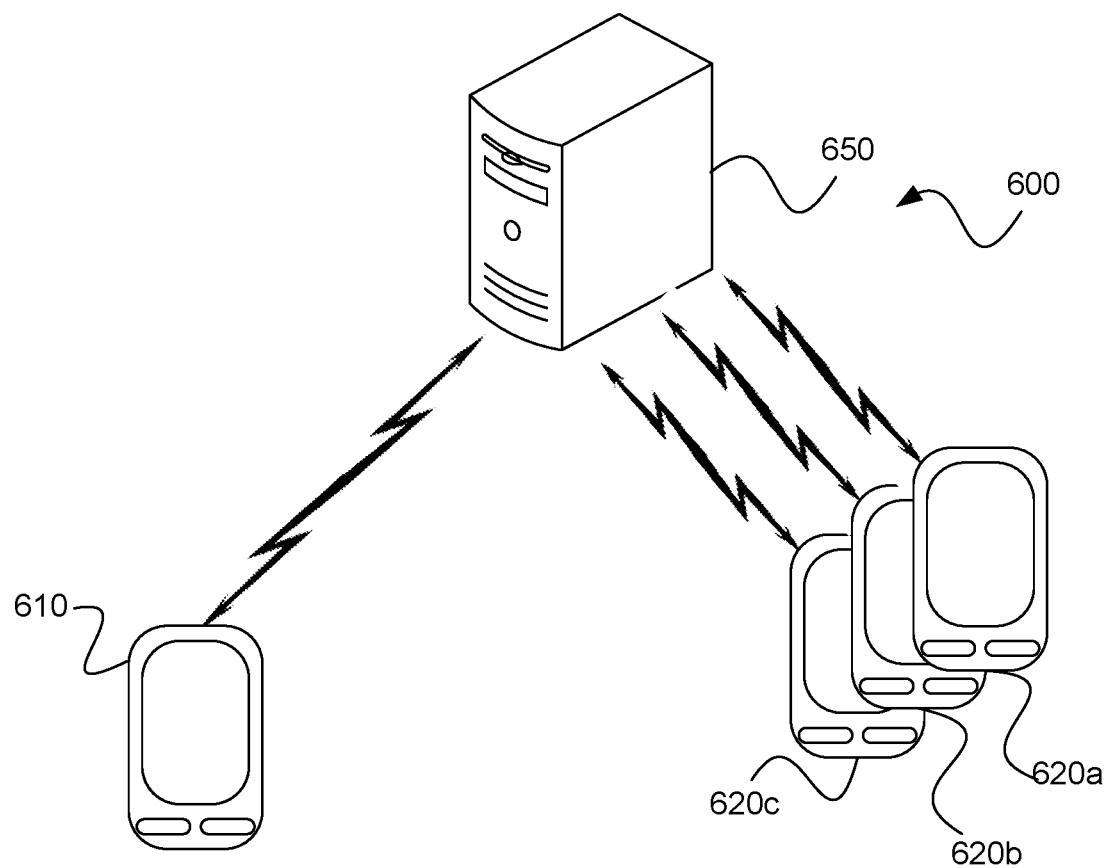
FIG. 6 is a schematic general view of a communication system according to one embodiment of the teachings herein.

FIG. 6 shows a schematic overview of a communications system 600 according to an embodiment herein. A mobile communication terminal 610, 620, such as the mobile communication terminals 100, 200 of FIGS. 1 and/or 2 is connected to a communications network (indicated by the arrows), for example the internet or a telecommunications network as per FIG. 5, for enabling communication between the various mobile communication terminals. In FIG. 6 there are four mobile communication terminals 610 and 620a-c. The communications system 600 may further comprise at least one server 650. The server is in one embodiment a server 300, 400 according to FIG. 3 or 4 and in one embodiment the server is a software module 250 implemented in a mobile communication terminal 100, 200 according to FIG. 1 or 2. In FIG. 6 only one server 650 is shown, but it should be noted that any number of servers 650 may be implemented in a communications system 600. Generally a server is a physical computer (a hardware system) or a software module dedicated to running one or more services (as a host), to serve the needs of users of the mobile communication terminals 610, 620 in the system 600.

In one embodiment the communications system 600 and/or the communications network of FIG. 6 forms part of the External Resources 520 of FIG. 5. And, in one embodiment, the communications network 500 of FIG. 5 forms part of the computer system 600 of FIG. 6. In these embodiments the mobile communication terminals 610, 620 of FIG. 6 correspond to mobile communication terminals 550 and 555 of FIG. 5.

As would be apparent to a skilled reader, a computer-enabled communications network, such as the Internet or a telecommunications network, provides many possibilities and variations of how to connect two terminals, and the embodiments disclosed herein are for purely exemplary purposes and should not be construed to be limiting.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other devices. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

Figure 7:
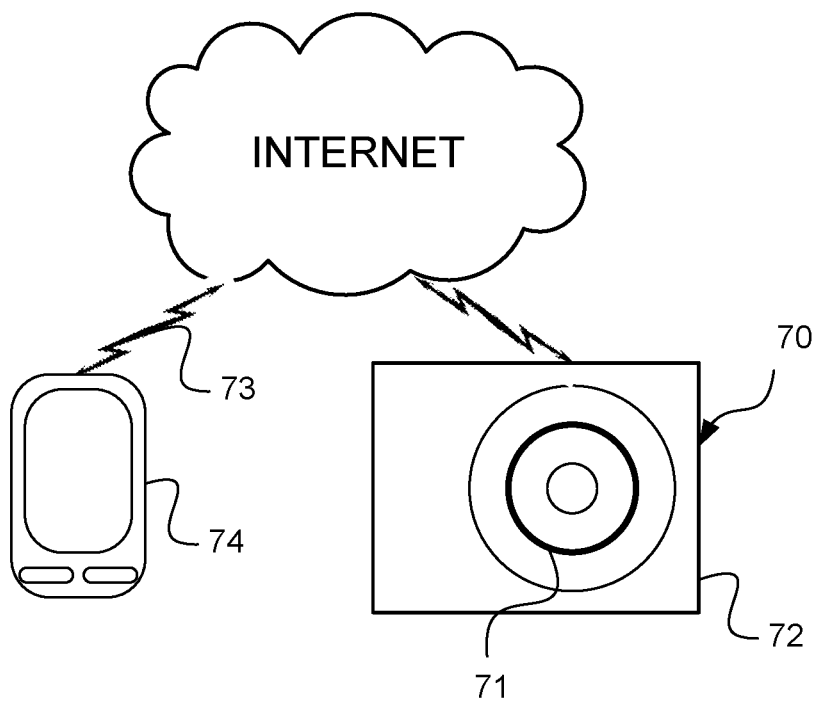
FIG. 7 shows a schematic view of a computer-readable medium according to one embodiment of the teachings herein.

FIG. 7 shows a schematic view of a computer-readable storage medium, such as a computer-readable storage medium, as described in the above. The computer-readable medium 70 is in this embodiment a data disc 70. In one embodiment the data disc 70 is a magnetic data storage disc. The data disc 70 is configured to carry instructions 71 that when loaded into a controller, such as a processor, executes a method or procedure according to the embodiments disclosed above. The data disc 70 is arranged to be connected to or within and read by a reading device 72, for loading the instructions into the controller. One such example of a reading device 72 in combination with one (or several) data disc(s) 70 is a hard drive. It should be noted that the computer-readable medium can also be other mediums such as compact discs, digital video discs, flash memories or other memory technologies commonly used.

The instructions 71 may also be downloaded to a computer data reading device 74, such as a mobile communications terminal 74 or other device capable of reading computer coded data on a computer-readable medium, by comprising the instructions 71 in a computer-readable signal 73 which is transmitted via a wireless (or wired) interface (for example via the Internet) to the computer data reading device 74 for loading the instructions 71 into a controller. In such an embodiment the computer-readable signal 73 is one type of a computer-readable medium 70.

The instructions may be stored in a memory (not shown explicitly in FIG. 7, but referenced 240 in FIG. 2) of the mobile communications terminal 74.

References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

Figure 8:
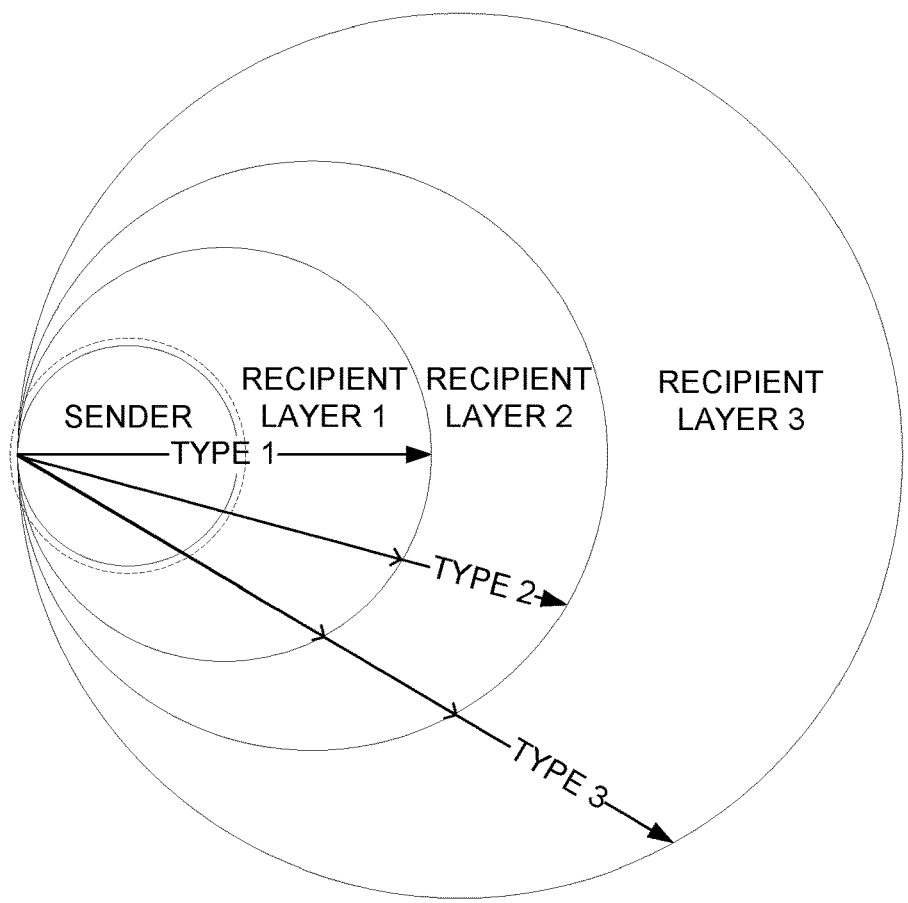
FIG. 8 shows a schematic view of such a hierarchical arrangement of a communication system according to one embodiment of the teachings herein.

To enable a smoother and easier communication between users of different mobile communication terminals, where one user may be a user that is cared for by the other users, the communication system 600 of FIG. 6 is arranged in a hierarchical structure where mobile communication terminals are arranged in different layers. Primarily there are two different types of layers, a sending layer and one or more receiving layers. FIG. 8 shows a schematic view of such a hierarchical arrangement of a communication system. The layering may be administered centrally by a server (possibly implemented as a software module in one mobile communication terminal) or distributed among the various devices in the communication system 600. In the example of FIG. 8, there is shown one sender layer SENDER) and three recipient layers RECIPIENT LAYER 1, RECIPIENT LAYER2, RECIPIENT LAYER3.

As in any communication system, the various devices are configured to communicate with one another by sending messages. To enable for a smooth and efficient message sending allowing a user or SENDER to select a message and its recipients quickly and without technical knowledge or much knowledge of communication systems, at least a portion of the messages that may be sent in the communication system is arranged with a message type. In FIG. 8, there are three different types being shown, TYPE 1, TYPE 2, and TYPE 3. The layering of the recipients is associated with different types of messages so that a message handler (not shown in FIG. 8, but will be discussed in detail in the below) may select recipients for a message based on the type of message. As is indicated by the dashed circle around the sender layer SENDER in FIG. 8, the sender user may not be aware of who the users are in the recipient layers RECIPIENT LAYER X. A user sending a message would then not need to know, select or concern himself with who the actual recipient of the message is which simplifies generation and sending of the message as no recipient needs to explicitly selected or indicated by the sender SENDER.

The recipient layers (RECIPIENT LAYER X) may be generated based on a phonebook or other contact list stored in the sender mobile communication terminal (referenced 610 in FIG. 6) or in a recipient mobile communication terminal (referenced 620 in FIG. 6). Alternatively or additionally, the recipient layers may be generated based on group listings in social media applications.

A recipient layer may comprise more than one user or recipient and as a recipient layer is selected based on a message type, all recipients in the selected recipient layer may be selected as recipients or a subset, possibly being only one recipient, may be selected as recipient.

The messages may be generated based on a pre-specified type. In this manner a user may simply select a message type from a number of predefined message types and a message is automatically generated and possibly also sent by the user issuing a single simple command such as pressing a virtual key.

Alternatively or additionally, the type of a message being or already generated may be determined based on the content of the message. This allows a user to generate a message without knowing the different available types by simply typing in or otherwise generating his message (for example by selecting keywords or following instructions in a message generating wizard or form) and the message is then sent to a recipient layer based on the information in the message.

Even though FIG. 8 only shows three different types of messages (TYPE 1, TYPE 2, TYPE 3, it should be noted that more than one type of message may be sent to the same recipient layer.

Message types TYPE X may be prioritized in such a manner that a higher prioritized message (TYPE 1 for example) may only be sent to high level recipient layers (RECIPIENT LAYER 1 for example), whereas a lower prioritized message (TYPE 1 for example) may be sent to the corresponding low level recipient layers (RECIPIENT LAYER 3 for example) as well as to higher recipient layers (RECIPIENT LAYERS 1 and 2 for example). This is indicated in FIG. 8 by the arrows for message types 2 and 3 having smaller arrows when intersecting the upper layers, layers 1 and 2.

It should be noted that more than one type may be associated with each or any recipient layer even though the figures only show three different message types.

In one embodiment the messages are communication requests and the types are communication request types. For handling communication requests it is beneficial to a user if he need not know or find out exactly to whom a communication request has to be sent to, especially as a user is often not concerned with who executes a communication request, only that the communication request is answered and executed. The sending user thus only have to focus on selecting a proper communication request and the communication system will handle the rest including selecting recipients and transmitting the communication request.

Figure 9:
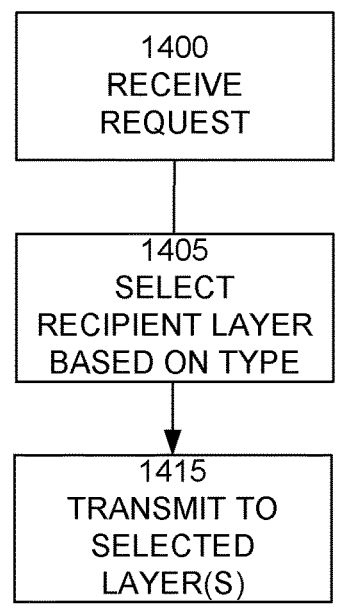
FIG. 9 shows a general flowchart for a method of selecting a recipient based on a recipient layer model according to one embodiment of the teachings herein.

FIG. 9 shows a general flowchart for a method of selecting a recipient based on the recipient layer model of FIG. 8. A communication request or other message is received 1400 by a message handler being implemented in a server (for centralized control) or a message handler application (250) (for distributed control). It should be noted that the steps may be performed in unison by one and the same apparatus, for example the server, or some actins may be executed by one apparatus, and other actions executed or performed by another apparatus. The same is true for all flow charts disclosed herein.

As the communication request has been received a recipient layer is selected 1405 based on the message type and the communication request is transmitted to the selected layer(s) 1415. As noted in the above, a message or communication request type may be associated with more than one layer.

Figure 10:
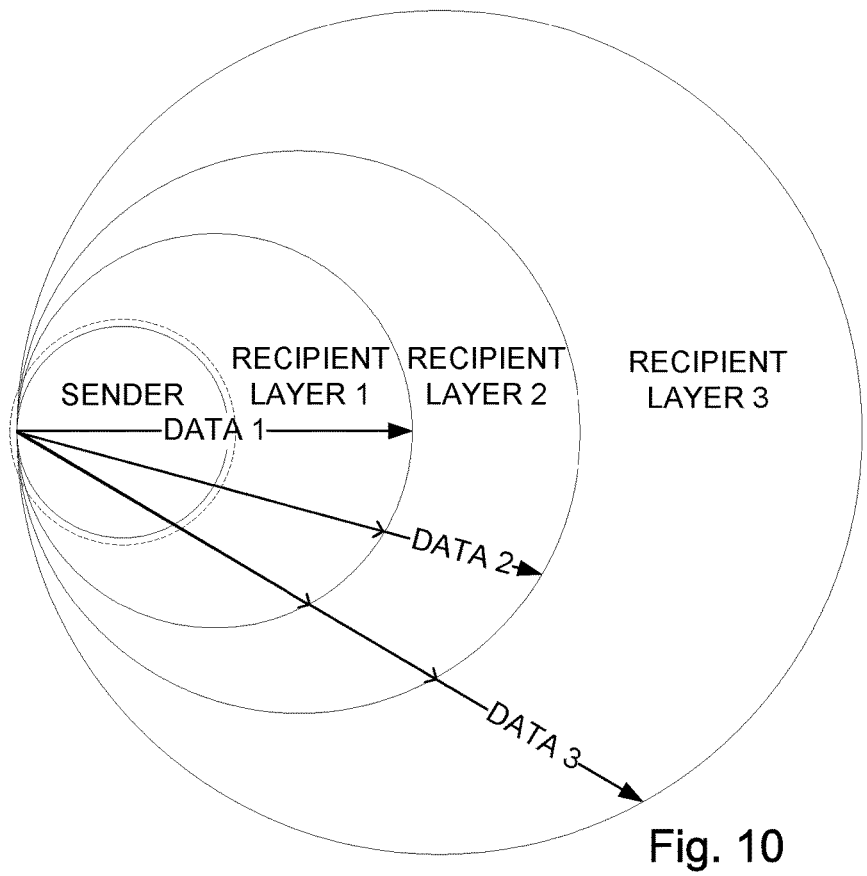
FIG. 10 shows a schematic view of how data levels are associated with or cleared for different recipient layers according to one embodiment of the teachings herein.

In one embodiment a message type may also be associated with a data structure possibly having or indicating different data levels and the different recipient layers may be cleared for different data levels. FIG. 10 schematically shows how such data levels are associated with or cleared for the different recipient layers. For example, the highest recipient layer RECIPIENT LAYER 1 illustrated as the innermost layer in FIG. 10, is associated with a high data level DATA 1, the middle recipient layer RECIPIENT LAYER 2, is associated with a middle data level DATA 2, and the lowest recipient layer RECIPIENT LAYER 3 illustrated as the outermost layer in FIG. 10, is associated with a low data level DATA 3. For the purpose of this application a higher layer will refer to a layer having a higher priority or clearance or a stronger association with the sender, and a lower layer will refer to a layer having a lower priority or clearance or a weaker if any association with the sender.

This enables data to be filtered and sorted based on the message type which enables a sender to not have to worry about or indicate what data is sent to which recipient.

Figure 11:
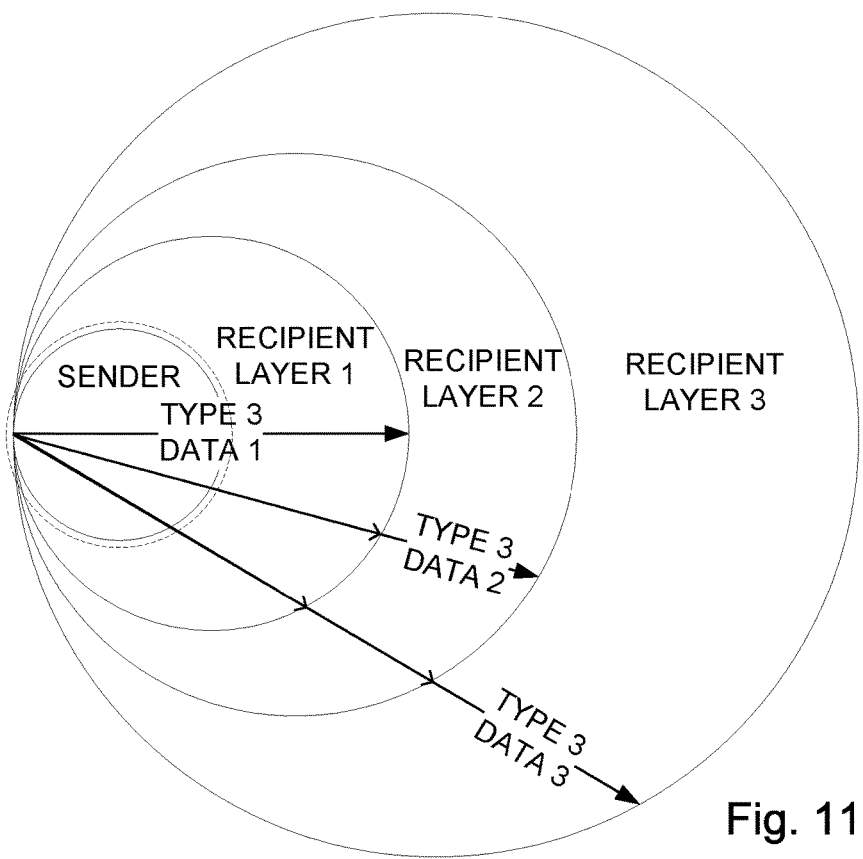
FIG. 11 shows a schematic view of such a hierarchical arrangement according to one embodiment of the teachings herein.

As one communication request type may be sent to more than one layer, it can be good to filter the data that is shown or transmitted to the different recipient layers to enable for a hierarchical data layering as well. The teachings herein thus provide for a manner in which a user may send a request to multiple recipients without having to know who the recipients are and what data to send to each recipient. FIG. 11 shows a schematic view of such a hierarchical arrangement. In this example a message having a request type TYPE 3 is sent to all recipient layers, but the data being transmitted to the various recipient layers has been filtered based on the recipient layer which in turn is based on the request type, thereby implementing a filtering based on the type. In the example of FIG. 11 a message is sent to RECIPIENT LAYER 1 with DATA 1, to RECIPIENT LAYER 2 with DATA 2 and to RECIPIENT LAYER 3 with DATA 3.

One example of different data levels is for a medical application, wherein the data levels are arranged in the following: [LAYER 3: CRUCIAL MEDICINES; LAYER 2: ALL MEDICINES; LAYER 1: MEDICINES AND REASON/ILLNESS]. Another example of different data levels is for a confidential data application, wherein the data levels are arranged in the following: [LAYER 3: TIMELIMITS AND ACTIONS; LAYER 2: ALSO SUBJECT MATTER; LAYER 1: ALSO PROPOSED ACTION].

Figure 12:
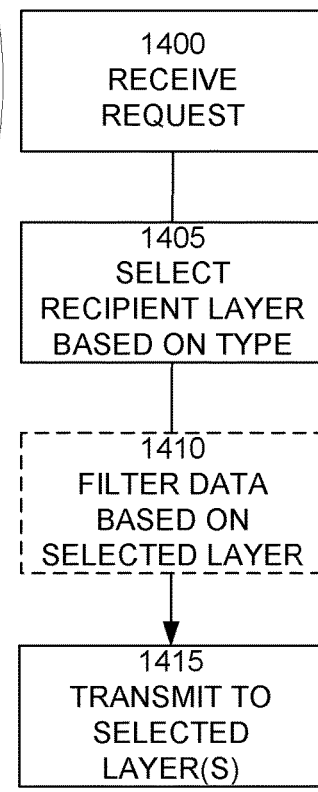
FIG. 12 shows how a method according to herein is expanded with the optional filtering based on data according to one embodiment of the teachings herein.

FIG. 12 shows how the general flowchart of a method according to herein is expanded with the optional filtering based on data. The filtering is optional as is indicated by the dashed lines.

Figure 13:
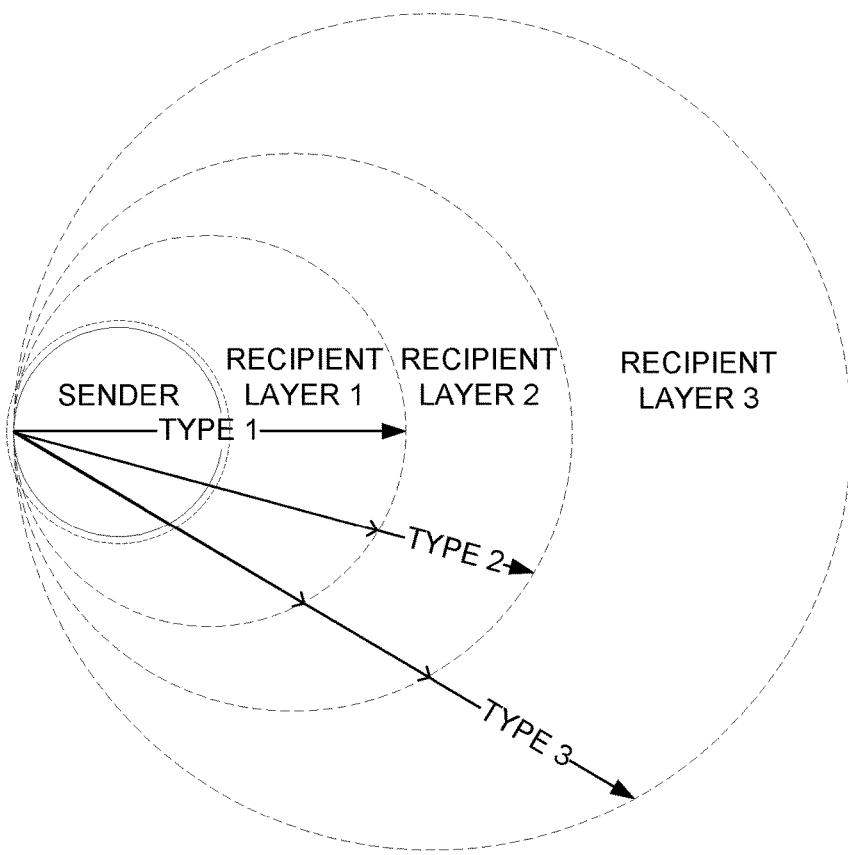
FIG. 13 shows a schematic view of a transparent recipient layer architecture according to one embodiment of the teachings herein.

As has been noted in the above, the sender may not be aware of who is in the various recipient layers and in a similar manner the different recipients in the different recipient layers may not know who is in the other recipient layers. This simplifies the inter-recipient layer communication. The recipient layers may also be transparent with regards to the recipients in each recipient layer. FIG. 13 shows a schematic view of a transparent recipient layer architecture.

A message handler has been discussed in the above to be able to receive a communication request and direct it according to its type. The message handler may be implemented centrally in a server (possibly as a software module) or distributed wherein different devices or apparatuses are configured or arranged to implement sub functionalities of the message handler.

Figure 14:
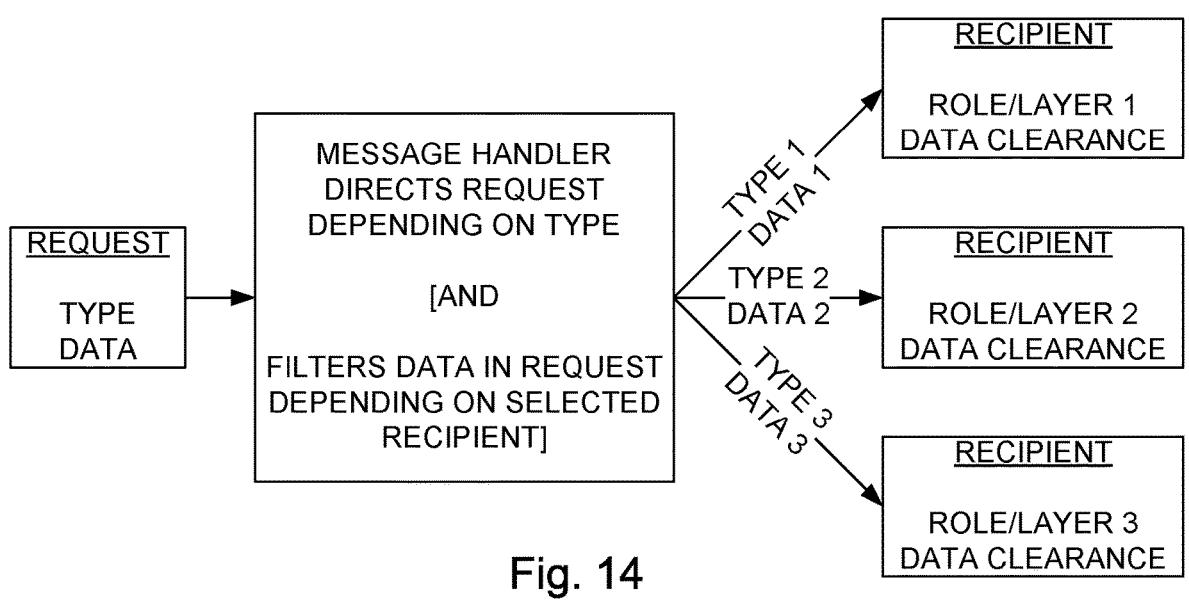
FIG. 14 shows a schematic view of the functionality of a message handler according to one embodiment of the teachings herein.

FIG. 14 shows a schematic view of the functionality of the message handler, wherein a REQUEST or other message is received, which communication request carries or may be determined to be of a type TYPE. Optionally the communication request also carries data DATA. The message handler selects a recipient layer (and thereby a recipient) based on the message type, possibly after having determined the message type, and optionally filters the data depending on the selected recipient and then directs or transmits the communication request accordingly. The message handler may be implemented to only direct the message/communication request and another module may then carry out the actual transmittal of the message/communication request or the message handler may also transmit the message as a recipient has been selected.

Figure 15:
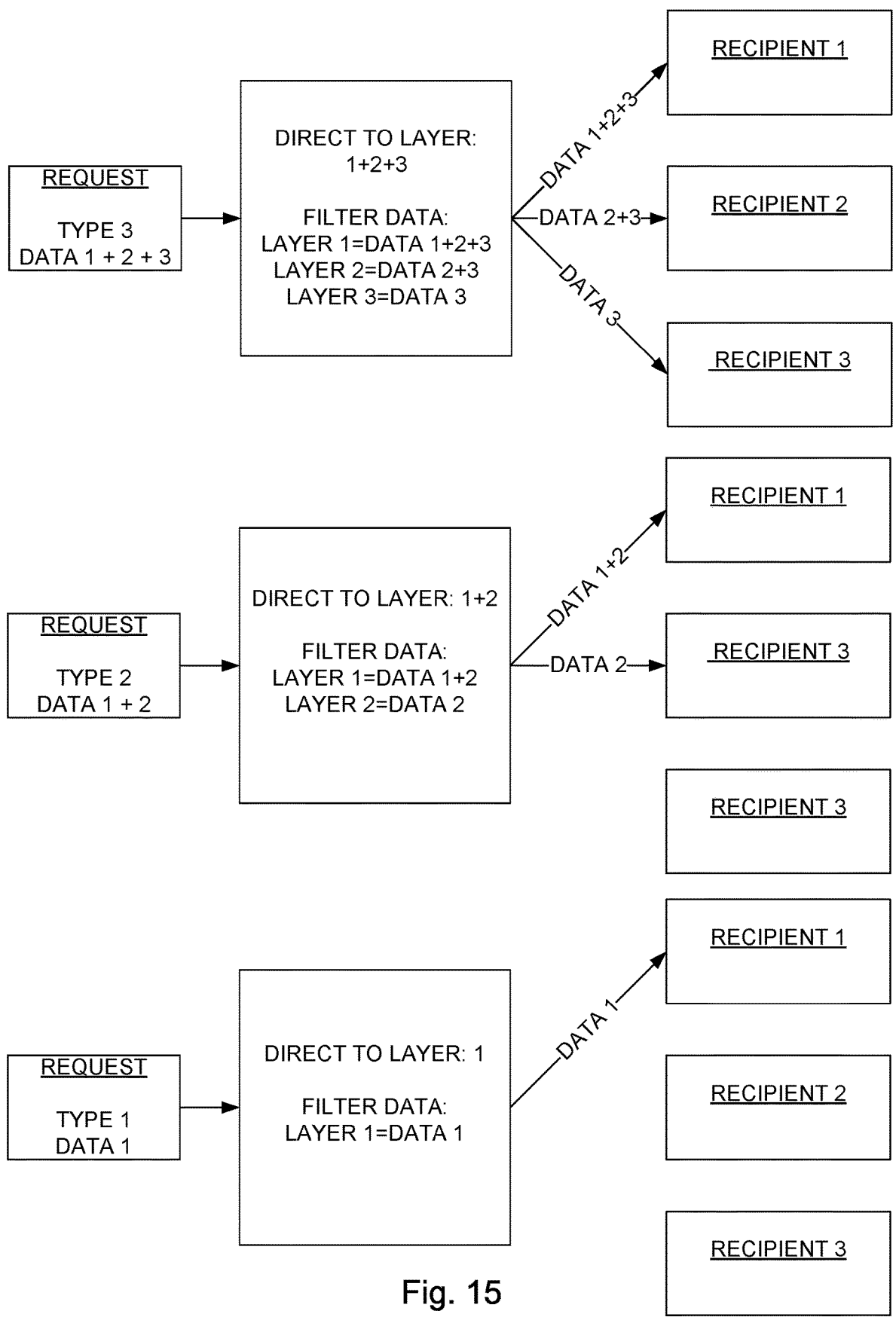
FIG. 15 shows a schematic view of how a message handler directs and filters different types of messages according to one embodiment of the teachings herein.

FIG. 15 shows a schematic view of how the message handler directs and filters different types of messages. In the example of FIG. 15, three different communication requests are being handled, one of TYPE 1, carrying data for RECIPIENT LEVEL 1, one of TYPE 2, carrying data for RECIPIENT LEVEL 1 and RECIPIENT LEVEL 2 and one of TYPE 3, carrying data for RECIPIENT LEVEL 1, RECIPIENT LEVEL 2 and RECIPIENT LEVEL 3. The various communication requests are transmitted to the selected recipients based on the request type and carries the data associated with the corresponding recipient layers.

Figure 16:
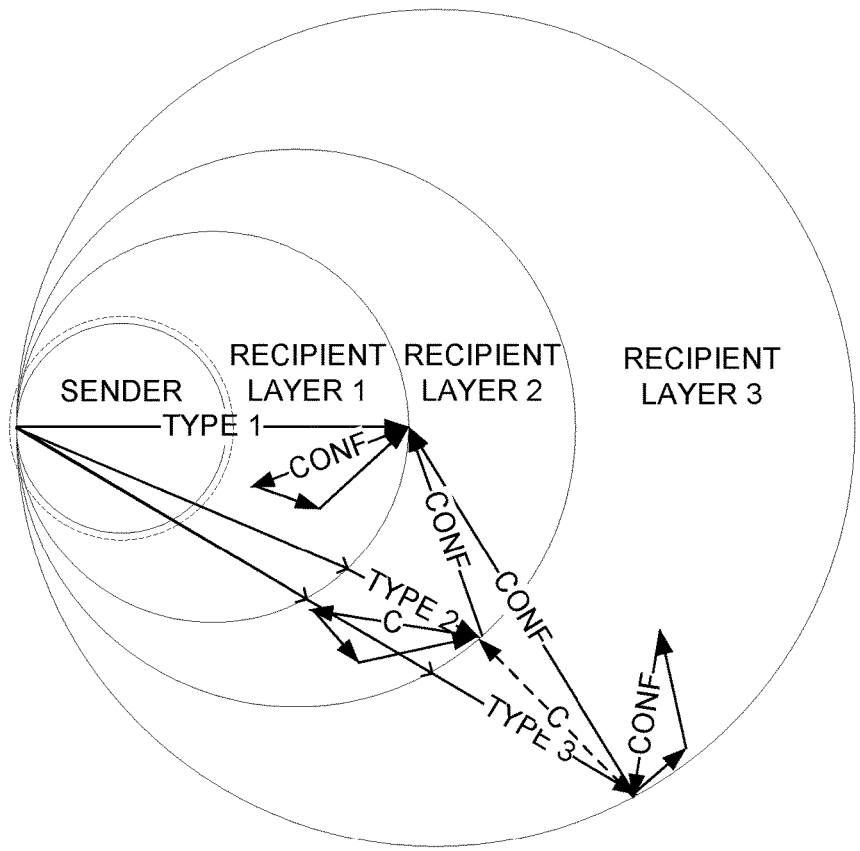
FIG. 16 shows a schematic view of a recipient layer hierarchy wherein confirmation that a communication request has been received or accepted and/or possibly carried out is transmitted from a recipient according to one embodiment of the teachings herein.

As a communication request or message may be sent to more than one recipient in each recipient layer there is a risk that the recipients do not know who should deal with a specific communication request or if the communication request has already been dealt with. Also, a recipient needs to be informed that a communication request actually has been handled so that the recipient need not worry about it anymore. Also, to prevent that a communication request is forgotten and to prevent such double work a manner to confirm a communication request is presented in FIG. 16 showing a schematic view of a recipient layer hierarchy wherein confirmation that a communication request has been received or accepted and/or possibly carried out is transmitted from a recipient. The confirmation (referenced CONF or C in FIG. 16) may be transmitted directly to the other recipients in the recipient layer, or to a message handler for forwarding to the other recipients. A confirmation may also be sent to other recipient layers as is indicated in FIG. 16.

Figure 17:
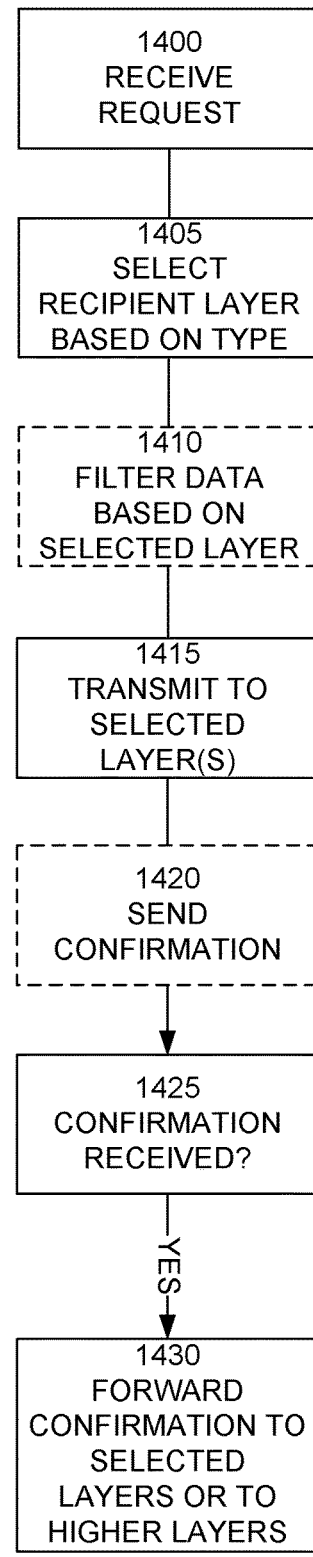
FIG. 17 shows a flow chart of how a general method according to herein is expanded by the added functionality of sending confirmations according to one embodiment of the teachings herein.

FIG. 17 shows a flow chart of how the general method according to herein is expanded by the added functionality of sending confirmations.

As a communication request has been transmitted the recipient sends a confirmation 1420. This transmission is indicated with dashed arrows as it may be executed by a different device than the one(s) executing the rest of the method. As a confirmation is received 1425 the confirmation may be forwarded 1430 to selected layers or to higher layers so that the higher layers are informed of the progress of a communication request. It should be noted that the forwarding 1430 may be included in the sending of the confirmation 1420 if a recipient sends his confirmation directly to other recipients. Combinations are also possible.

In one embodiment the highest recipient layer RECIPIENT LAYER 1, is informed of the status or progress of all communication requests by receiving (a copy of) every communication request and also receiving (a copy of) every confirmation.

In one embodiment the message handler is configured to resend a communication request if no confirmation is received. This may be done automatically or after prompting by a recipient in a higher recipient layer, for example in RECIPIENT LAYER 1. Such prompting is then received by the message handler and acted upon.

The message handler may alternatively be arranged to send out a reminder of the communication request. A reminder is beneficial in that it usually requires less bandwidth to be transmitted and also avoids resending possibly sensitive data.

Resending the communication request is beneficial in that a recipient will know what the communication request relates to—especially beneficial if the original communication request was simply not received.

Optionally a higher level recipient or the message handler can select a new recipient layer from a lower level if no confirmation has been received. This would ensure that a communication request is handled, since a larger recipient group is targeted.

Figure 18:
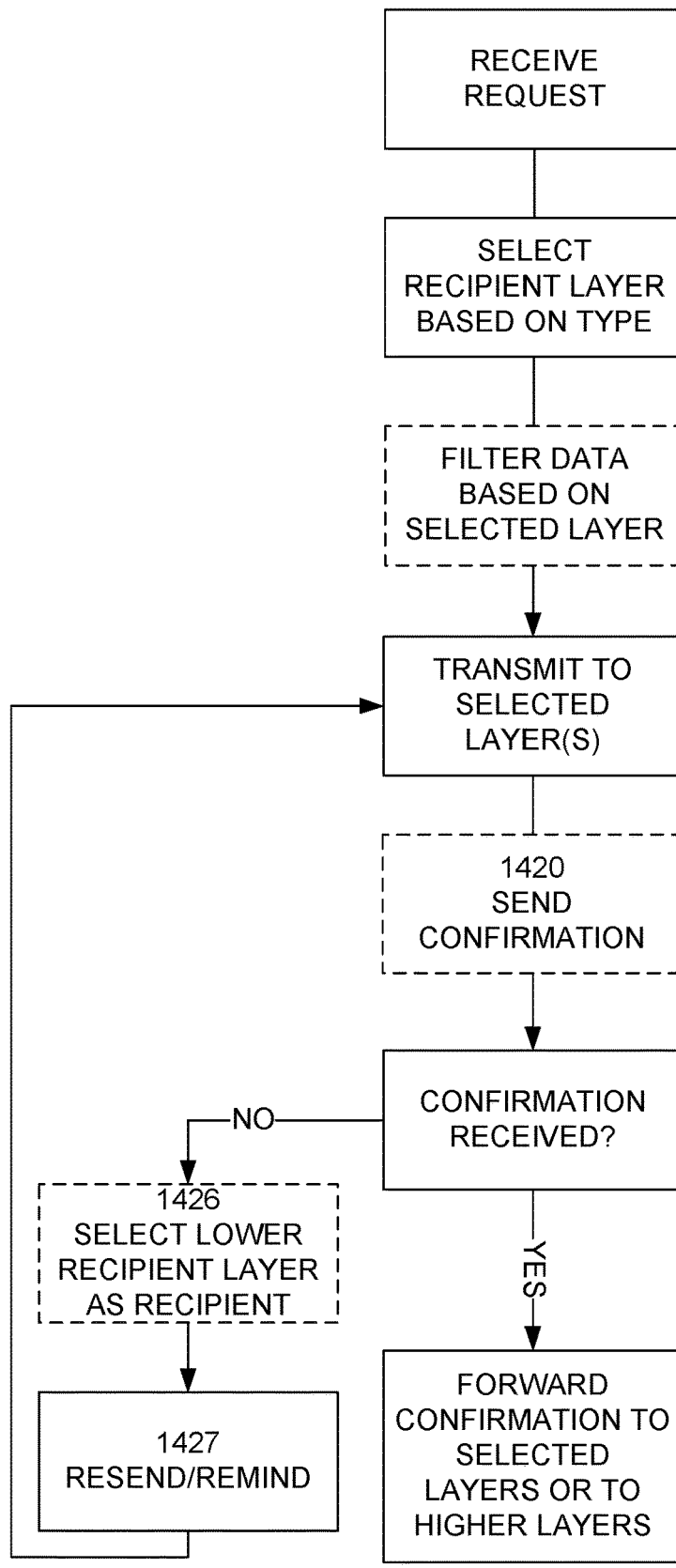
FIG. 18 shows a flow chart of how a general method according to herein is expanded by the added functionality of resending confirmations when no confirmations are received according to one embodiment of the teachings herein.

FIG. 18 shows a flow chart of how the general method according to herein is expanded by the added functionality of resending confirmations when no confirmations are received. If no confirmation is received, a new recipient layer may optionally be selected 1426 (as is indicated by the dashed lines) and a reminder is transmitted or the communication request is retransmitted. Alternatively a reminder may be sent out to those recipients who have already received the communication request and the communication request is resent to those that have not received it yet.

To ensure that a communication request is handled a higher level recipient may choose to delegate or distribute a communication request by deflecting or forwarding a communication request to a lower recipient layer.

As the recipient forwards or deflects a communication request any data carried in the communication request may be filtered based on the recipient layer to be forwarded to, or the communication request is forwarded as it was received.

Figure 19:
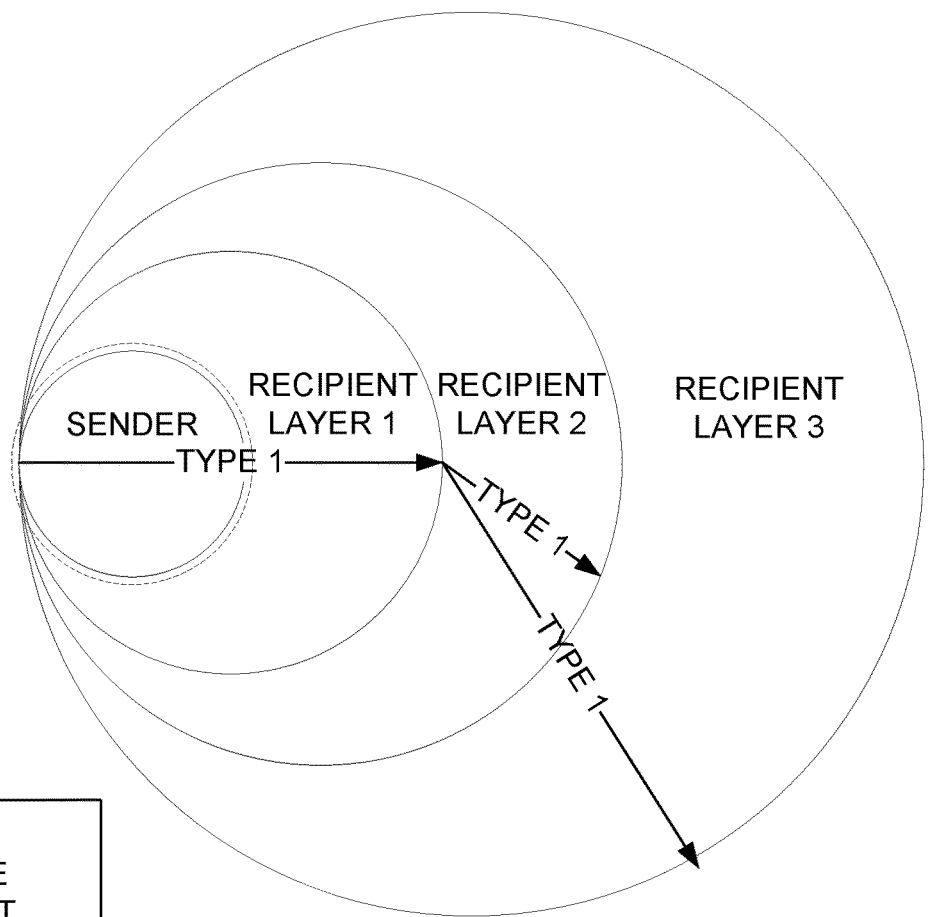
FIG. 19 shows a schematic view of a recipient hierarchy and how a message/communication request may be deflected or forwarded according to one embodiment of the teachings herein.

FIG. 19 shows a schematic view of the recipient hierarchy and how a message/communication request may be deflected or forwarded.

The difference between a forwarded and a deflected message for the content of this application is that a deflected message or communication request will not be handled by the original receiver, whereas a forwarded communication request/message may be handled by any recipient. By deflecting a message, the user thus delegates the communication request/message to someone else, whereas by forwarding it the recipient simply expands the number of recipients.

Figure 20:
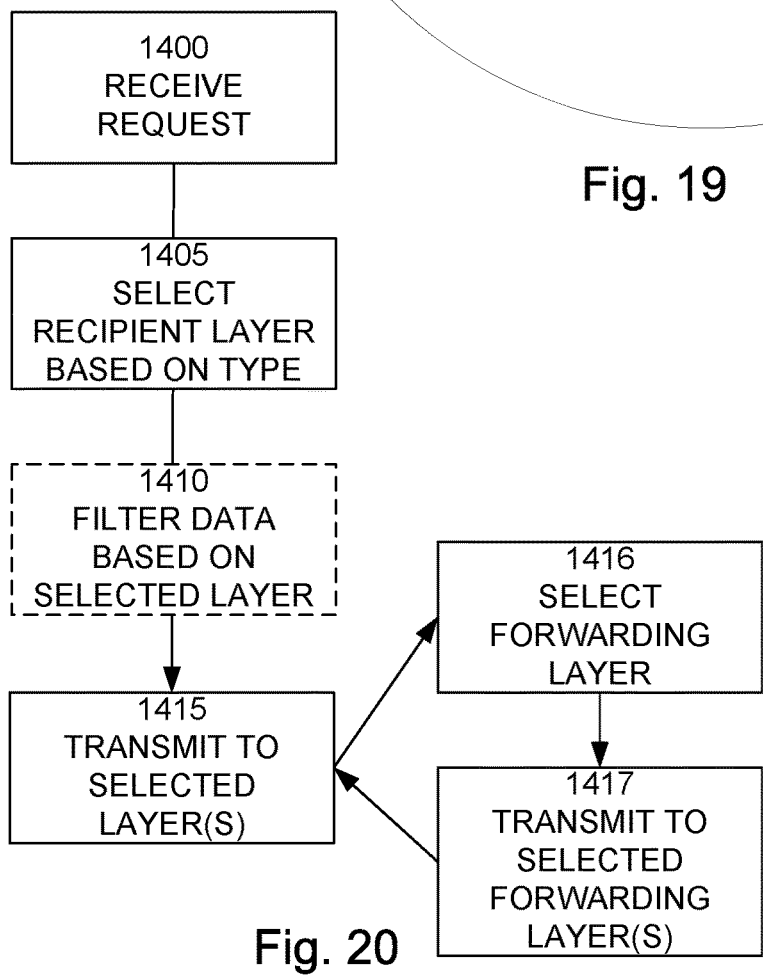
FIG. 20 shows a flow chart of how the general method according to herein is expanded by the added functionality of forwarding or deflecting a message or communication request according to one embodiment of the teachings herein.

FIG. 20 shows a flow chart of how the general method according to herein is expanded by the added functionality of forwarding or deflecting a message or communication request. As a communication request or message is to be forwarded or deflected a recipient layer is selected 1416. This may be selected automatically by a further association of a message type and a recipient layer. Alternatively, a recipient may indicate to which recipient layer the communication request or message should be forwarded/deflected. Then the message/communication request is forwarded or deflected 1417.

Figure 21:
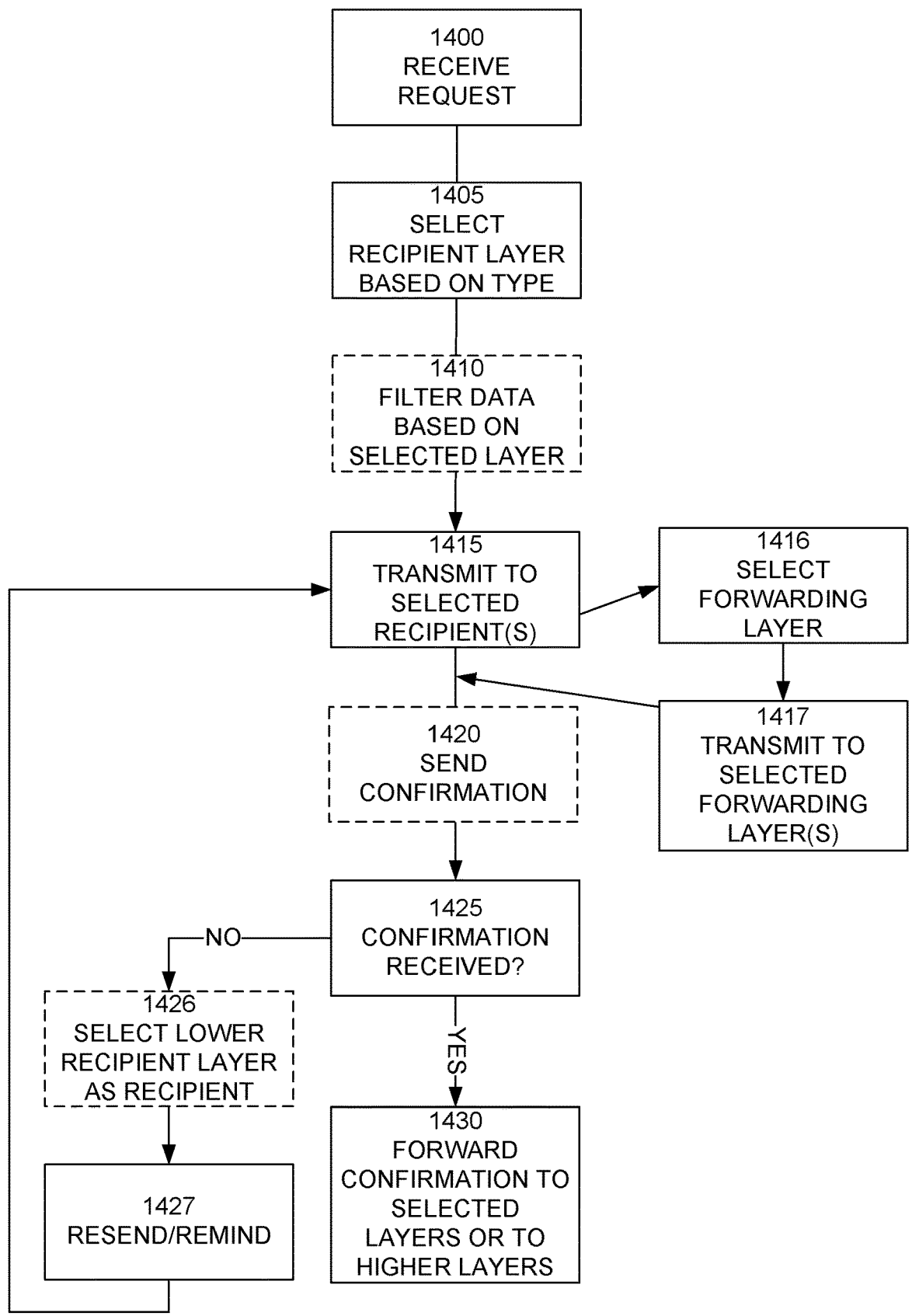
FIG. 21 shows a flow chart of a general method according to one embodiment of the teachings herein.

FIG. 21 shows a flow chart of a general method according to herein encompassing all features disclosed in the above.

To ensure that a communication request is not sent to a recipient in vain, the distance to the recipient may be taken into account when selecting a recipient layer. If the communication request requires physical interaction, sending the communication request to someone who will not be able to execute the communication request will be fruitless and only serve to delay the communication request and to increase the bandwidth in the system unnecessarily. To overcome such problems the message handler may be arranged to also select a recipient (layer) based on the distance of a recipient to the sender.

Figure 22:
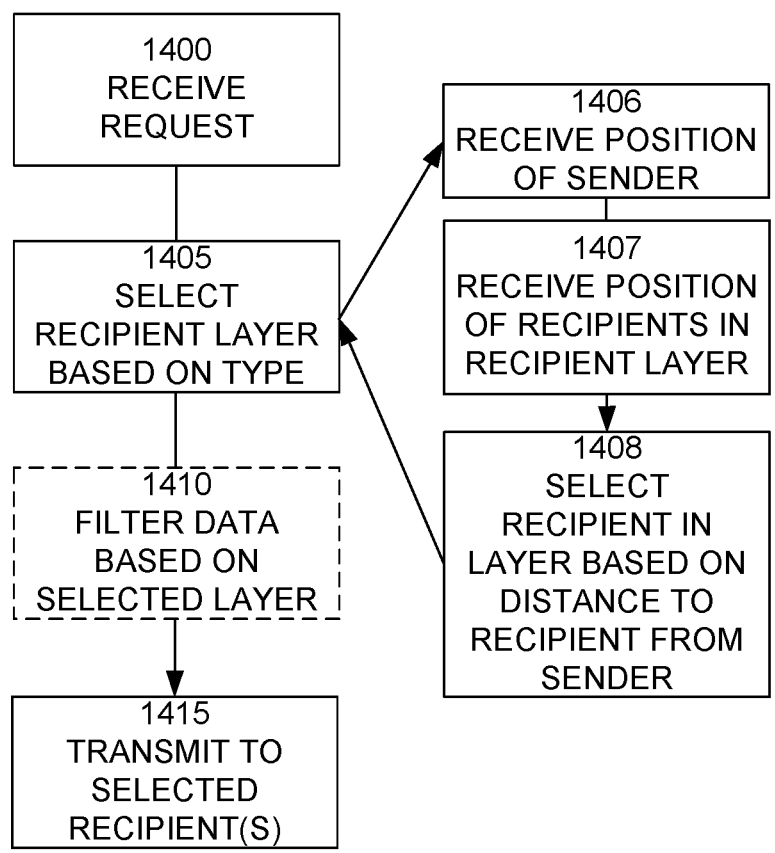
FIG. 22 shows a flow chart of how a general method according to herein is expanded by the added functionality of selecting a recipient in a recipient layer based on the distance to the sender according to one embodiment of the teachings herein.

FIG. 22 shows a flow chart of how the general method according to herein is expanded by the added functionality of selecting a recipient in a recipient layer based on the distance to the sender. The message handler receives the position 1406 of the sending mobile communication terminal. The position may be received as part of the message or from a position determining device or by prompting the sending mobile communication terminal. The message handler also receives the position 1407 of potentially receiving mobile communication terminals in the selected recipient layer(s). The position may be received as part of the message or from a position determining device or by prompting the potentially receiving mobile communication terminal. At least one recipient in the recipient layer is then selected as recipient for the message or communication request.

If no recipient in the selected recipient layer is close enough a new recipient layer may be selected to ensure that the communication request can be handled by a recipient.

Figure 23:
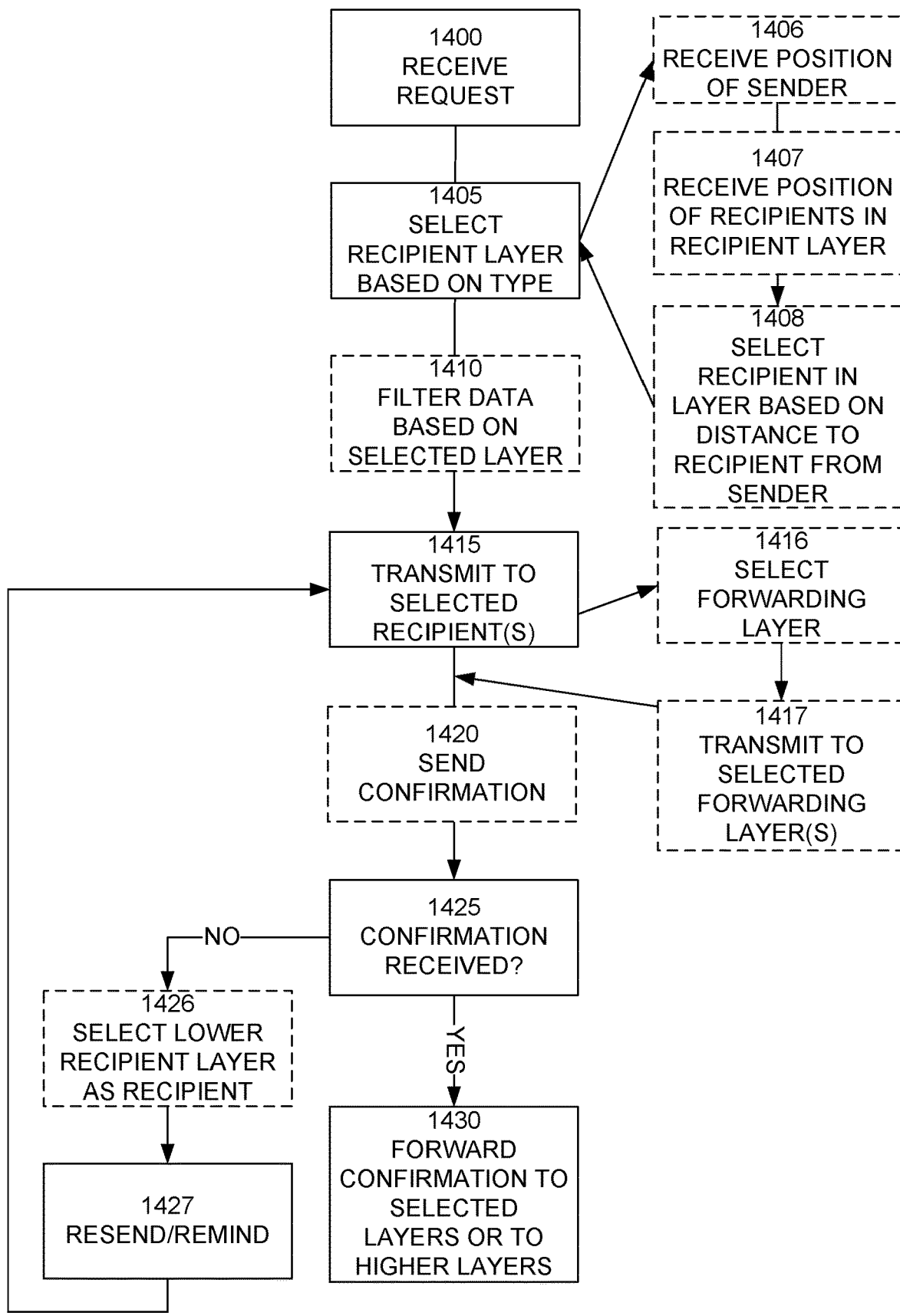
FIG. 23 shows a flow chart of a general method according to one embodiment of the teachings herein.

FIG. 23 shows a flow chart of a general method according to herein encompassing all features disclosed in the above, wherein some features are indicated to be optional.

EXEMPLARY EMBODIMENT

The teachings herein may for example be implemented in a telecare communication system for enabling a smoother communication between a person who is to be cared for, such as a senior, and those caring for the person cared for. As is known, many different persons may be involved in caring for a senior, such as immediate family, doctors, care givers, neighbours and volunteers to name a few. Of these many have different obligations and also attachments to the person cared for and will thus only be interested in or involved in certain types of communications. Also, not all persons involved should have access to all data that may be transmitted.

Figure 24:
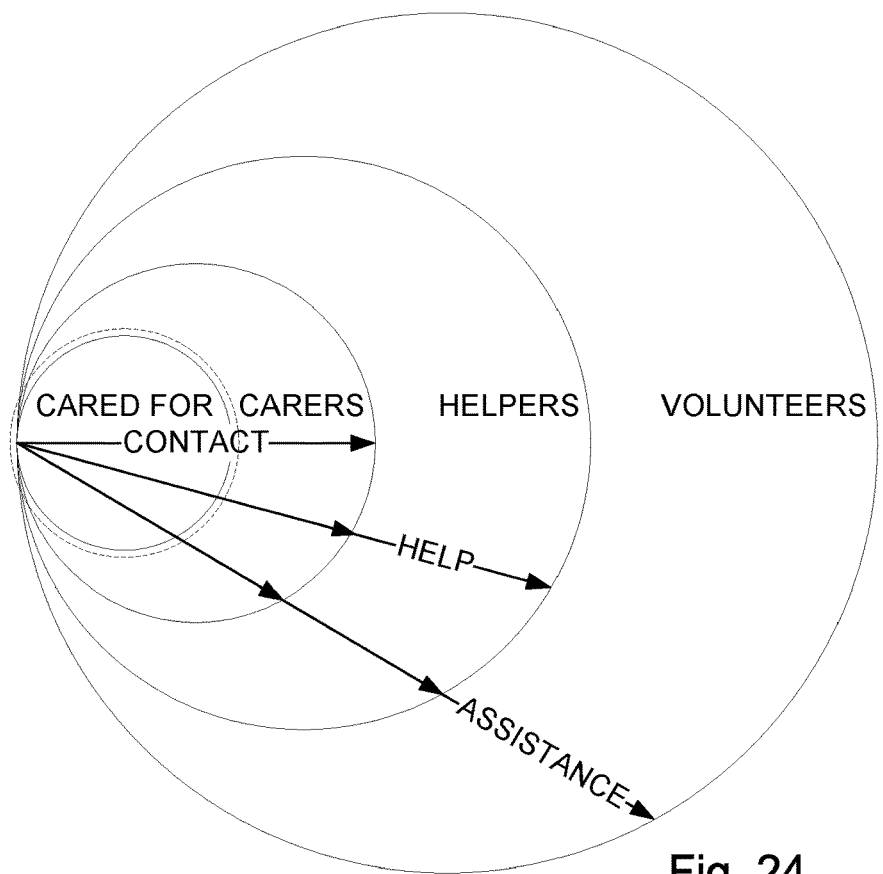
FIG. 24 shows a schematic overview of how a hierarchical arrangement may be used for a telecare communication system according to one embodiment of the teachings herein.

FIG. 24 shows a schematic overview of how a hierarchical arrangement such as disclosed in the above may be used for a telecare communication system. In this telecare communication system the SENDER is represented by the person cared for and is referenced CARED FOR.

The highest recipient layer RECIPIENT LAYER 1 is referenced CARERS and includes person(s) with close relation to the senior—in most cases relatives.

The middle recipient layer RECIPIENT LAYER 2 is referenced HELPERS and includes a (closed) network of friends often living close to the senior that agree to help when needed but without any direct responsibility to support. And the lowest recipient layer RECIPIENT LAYER 3 is referenced VOLUNTEERS and includes an (open) network of persons signed up to support any people in need of help when possible.

The different types of communication requests or message are, but are not limited to, a CONTACT request, a HELP request and an ASSISTANCE request. As has been indicated, other types of communication requests and messages are also possible, and will also be disclosed below.

A CONTACT request is a communication request for the closest layer (the CARER) to get in contact without the feeling of disturbing the "busy life" of the carer.

A HELP request is a communication request for the closest layer (the CARER) and the middle layer (the HELPER) to get some support, for example helping with a day to day life problem, such as closing a window or do some shopping. The HELP request may comprise data on what problem needs to be solved. Different data for different recipient layers may consist of sensitive information such as door codes or PIN numbers for credit cards.

An ASSISTANCE request is a communication request for assistance being an emergency request, and may be initiated for example through the press of a dedicated key on the mobile communication terminal. The emergency request is sent to CARERs and HELPERs and may also be sent to VOLUNTEERs if so specified in the message handler. The request may comprise a position of the cared for person and also an indication of the type of emergency and if any medicines or special competences are required.

One benefit of applying a communication system hierarchy as described herein to a telecare communication system is that the cared for person does not need to worry about who a communication request is sent to. As cared for person does not know who he is contacting, he may not be held back by fearing to be of nuisance. This is an important aspect for seniors in many modern cultures and as it is easier to place an anonymous request than a request to a specific person, the senior may utilize the telecare communication system more often and thus improve his quality of life. Furthermore, the system herein also enables the carer to receive updates on what requests are being made and if they are being handled and will thereby be at ease knowing that their loved one is cared for. Also, the telecare communication system as herein simplifies daily contact between a person cared for and the persons caring or supporting the person cared for through convenient communication, notification and request functions.

Another benefit is that a telecare communication system as herein helps protecting the integrity of a person cared for as data and other sensitive information is kept secret to certain recipients only and also as the telecare communication system allows for a protected identity of the recipients.

Figure 25:
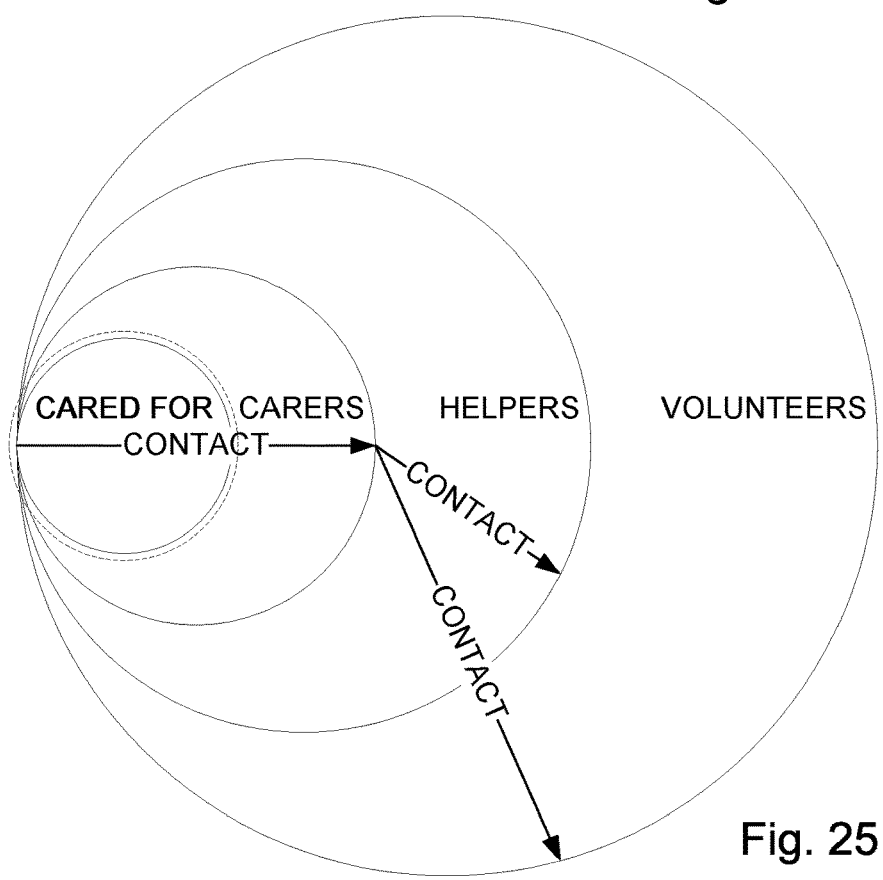
FIG. 25 shows a schematic overview of how a hierarchical arrangement such may be used for forwarding a request according to one embodiment of the teachings herein.

FIG. 25 shows a schematic overview of how a hierarchical arrangement such as disclosed in the above may be used for forwarding a request, wherein a CONTACT request is received by a CARER and forwarded to the HELPER recipient layer and/or the VOLUNTEER recipient layer.

Figure 26:
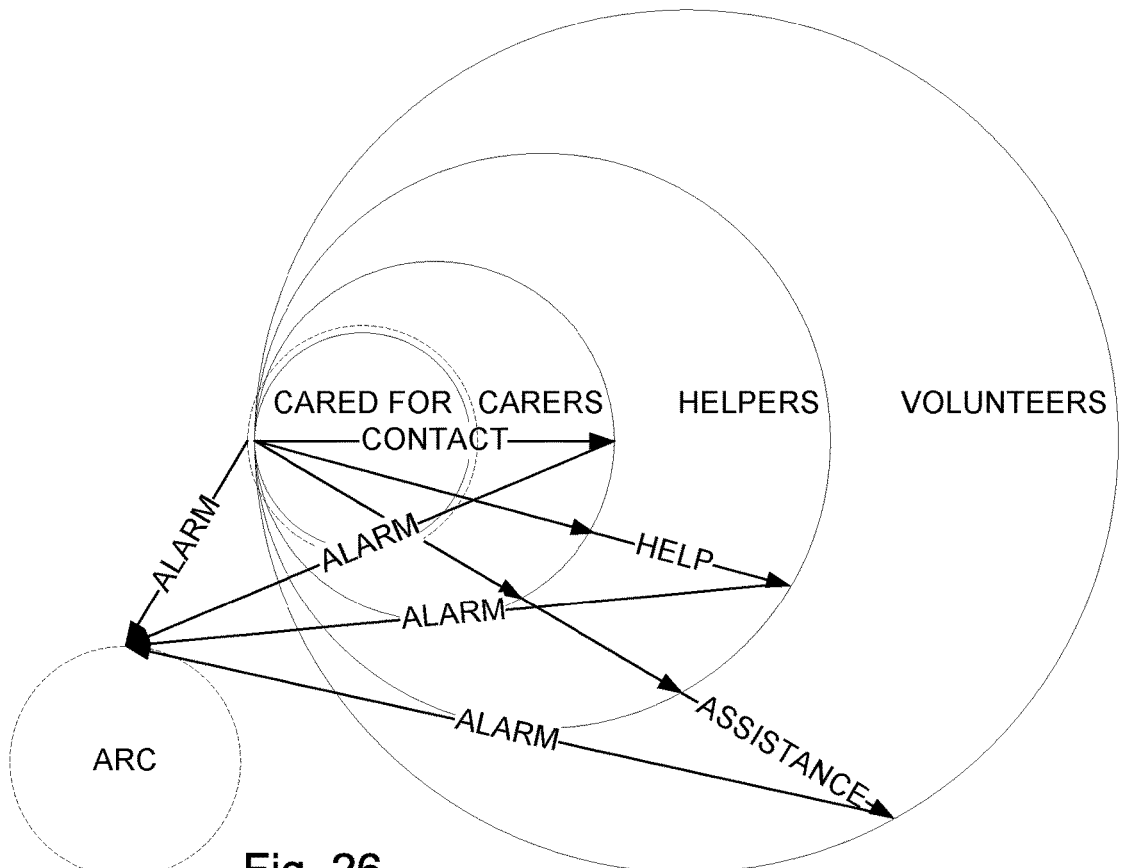
FIG. 26 shows a schematic overview of a telecare communication system hierarchy including an alarm center according to one embodiment of the teachings herein.

One recipient layer or a specific recipient may be an alarm service provider, such as an alarm center, that a recipient (or the sender) may choose to contact for further assistance. In FIG. 26, showing a schematic overview of a telecare communication system hierarchy including an alarm center, such as an alarm receiving center ARC which has been indicated to be outside the recipient layers, but it should be noted that the alarm center may be one recipient layer. Alarm requests may be initiated by both the sender and/or any recipient. An alarm request may be initiated at will or as a response to receiving a request as indicated in FIG. 26.

As has been disclosed for the assistance request, an alarm request may also be initiated from a dedicated key on the mobile communication terminal. However, an alarm request may also be generated through a press on a key in a separate alarm device, such as a panic button or an alarm accessory.

Figure 27:
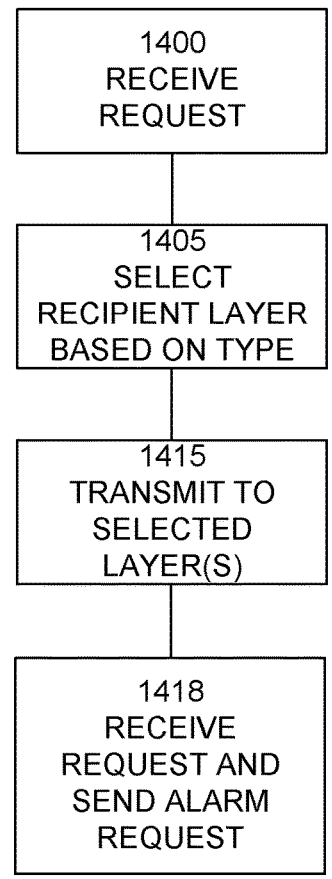
FIG. 27 shows a flowchart of how a general method according to herein may be expanded to include an alarm functionality according to one embodiment of the teachings herein.

FIG. 27 shows a flowchart of how a general method according to herein may be expanded to include this alarm functionality. As a communication request has been transmitted and received an alarm request is generated and transmitted 1418 to an alarm center.

Figure 28:
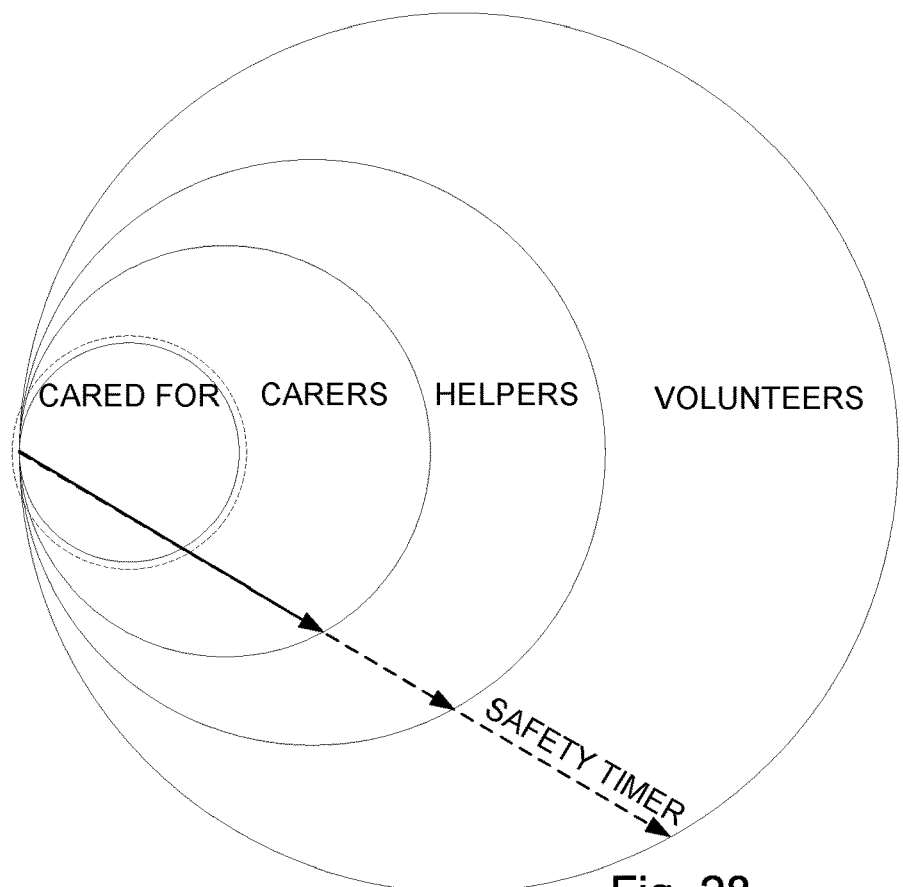
FIG. 28 shows a schematic overview of a telecare communication system hierarchy including a safety timer functionality according to one embodiment of the teachings herein.
Figure 29:
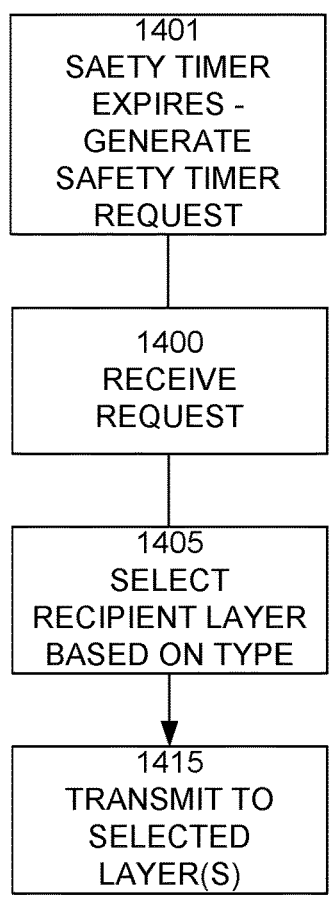
FIG. 29 shows a flowchart of how a general method according to herein may be expanded to include this safety timer functionality according to one embodiment of the teachings herein.

To allow for a closer monitoring of a person cared for, the telecare communication system may be equipped with a safety timer functionality. A safety timer is set, either by the person cared for or a recipient such as a carer, or other administrator, possibly even the alarm center, and as the safety timer expires without any actions have been taken by the person cared for a safety timer request SAFETY TIMER is transmitted to one or more of the recipient layers. An action that could be taken by the cared for person is to cancel or respond to a prompt that is generated and provided (such as displaying a pop up on the display of the mobile communication terminal). FIG. 28 shows a schematic overview of a telecare communication system hierarchy including a safety timer functionality and FIG. 29 shows a flowchart of how a general method according to herein may be expanded to include this safety timer functionality. As a safety timer is set and expires a safety timer request is generated 1405 and the safety timer request is received 1400 by the message handler.

Figure 30:
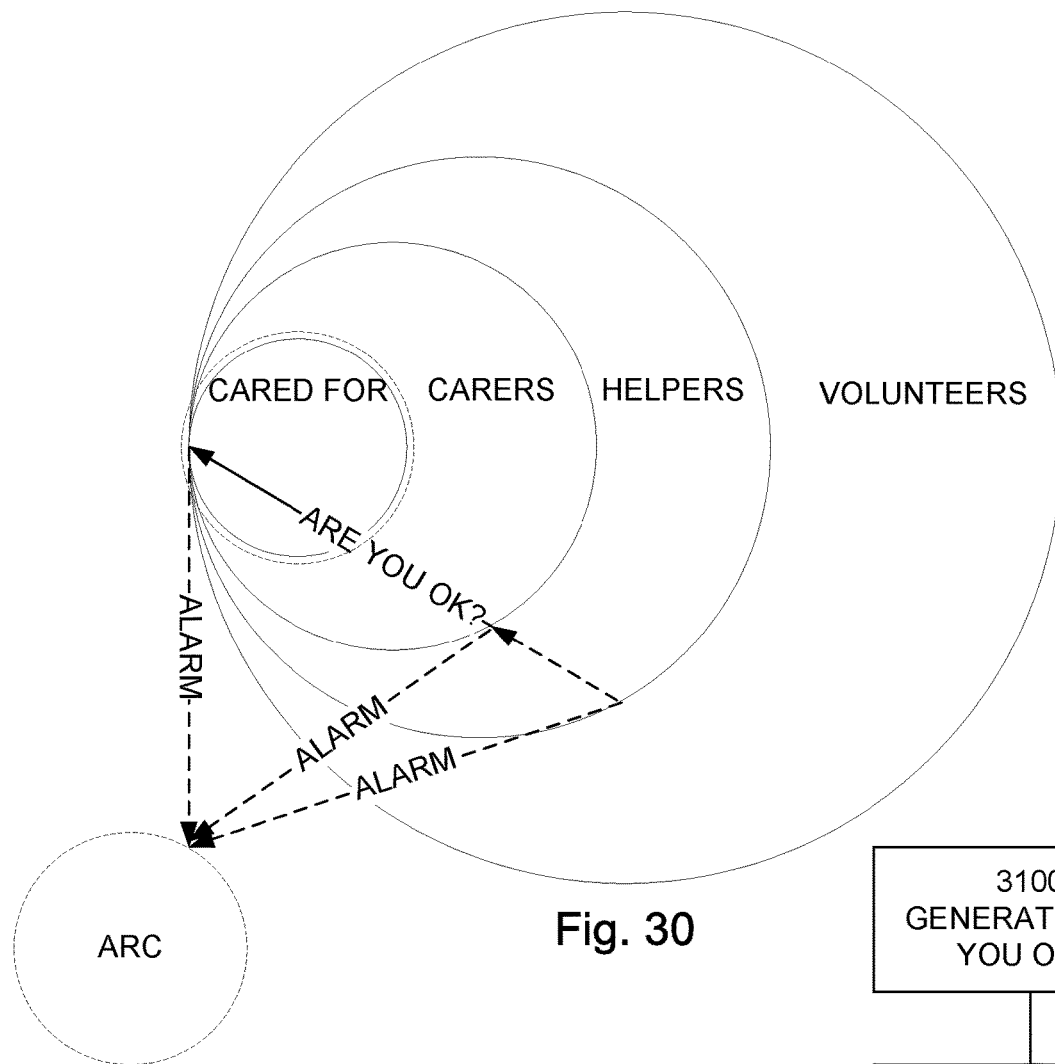
FIG. 30 shows a schematic overview of a telecare communication system hierarchy including an are you ok functionality according to one embodiment of the teachings herein.
Figure 31:
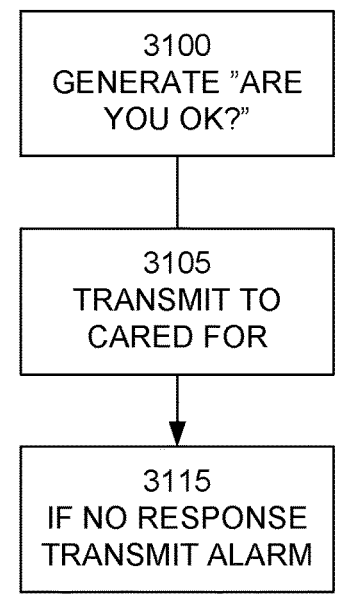
FIG. 31 shows a flowchart of how a general method according to herein may be expanded to include such an are you ok functionality according to one embodiment of the teachings herein.

To also enable for a closer monitoring of a person cared for, the telecare communication system may be equipped with a functionality for prompting a person cared for to determine whether the person cared for is experiencing or having any problems. A communication request requiring a response, an are you OK (ARE YOU OK?) request, is generated and transmitted by a recipient, such as a carer or a helper, or even an alarm center or a volunteer. Such a request may be sent sporadically (manually) or regularly (automatically). If no response is received, possibly within a timeout period, an alarm request may be generated and transmitted, possibly to the alarm center. FIG. 30 shows a schematic overview of a telecare communication system hierarchy including such are you ok functionality and FIG. 31 shows a flowchart of this prompting functionality. A prompting request (ARE YOU OK) is generated 3100 and transmitted to the person cared for 3105. If no response is received back from the person cared for an alarm request is generated and transmitted 3115.

Figure 32:
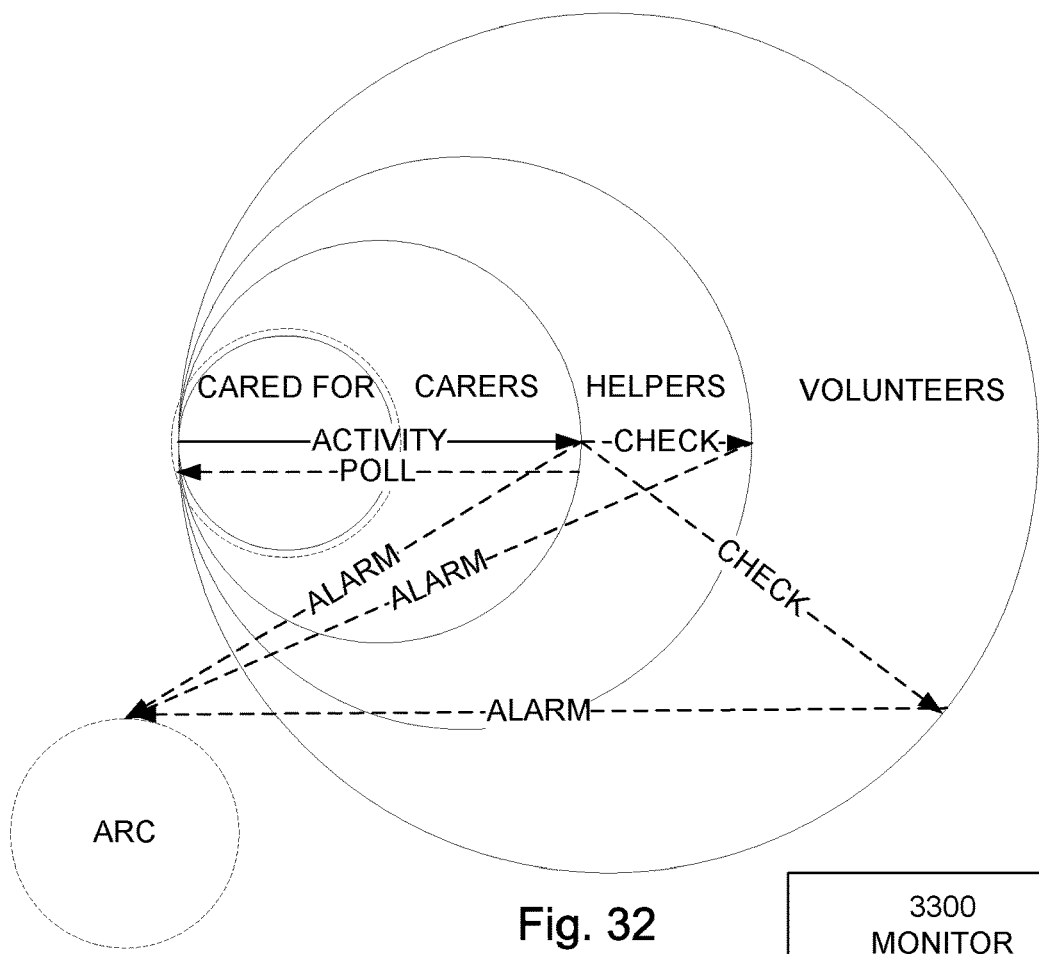
FIG. 32 shows a schematic overview of a telecare communication system hierarchy including a monitoring functionality according to one embodiment of the teachings herein.

A similar function is also enabled by a telecare communication system according to herein, namely to monitor the activity of a person cared for and if no activity is detected— or a specific activity is detected—an ACTIVITY message is generated and transmitted to a carer. The carer may then generate a request for an explanation or to check a status of the cared for person, such request asks for further information and is referenced POLL in FIG. 32 which shows a schematic overview of a telecare communication system hierarchy including such monitoring functionality. In one embodiment the POLL request is an ARE YOU OK request. As is also shown in FIG. 32, the carer may also generate and transmit requests asking a helper or a volunteer to check (a CHECK request) on the person cared for. If a carer or helper or volunteer determine that further assistance is required an alarm request may be generated and transmitted to an alarm center. In one embodiment the polling request is generated and transmitted automatically if no activity is detected or if a specific activity is detected as a response to the activity message. In one embodiment an alarm request is generated automatically in response to an ACTIVITY message for a specific activity, possibly such a demand for an alarm request is specified in the activity message.

In one embodiment the CHECK request may be generated automatically in response to determining that no response to a POLL request has been received, possibly within a time period.

One activity that can be monitored is the placement and acceptance of voice or video calls and if no voice calls or video calls are detected within a time period, an ACTIVITY request is generated. One activity that can be monitored is the sending and opening of messages and if no messages are detected within a time period, an ACTIVITY request is generated. One activity that can be monitored is the use of an application such as a browsing application and if an application is not used within a time period, an ACTIVITY request is generated. One activity that can be monitored is a movement of the mobile communication terminal of the person cared for and if no movement is detected within a time period, an ACTIVITY request is generated. One activity that can be monitored the network status of the mobile communication terminal of the person cared for, that is if the person is online or not, and if it is detected that a cared for person's mobile communication terminal is offline for a time period, an ACTIVITY request is generated. It should be noted that a combination of the activities may also be monitored within a same time period. The ACTIVITY request may comprise information on what activity has been monitored.

Figure 33:
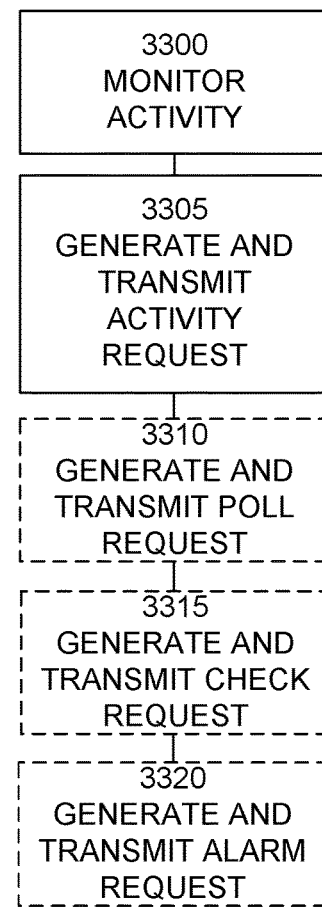
FIG. 33 shows a flowchart of a monitoring functionality according to one embodiment of the teachings herein.

FIG. 33 shows a flowchart of this monitoring functionality where an activity is monitored and based on such determination an ACTIVITY request is generated and transmitted 3305. This may be done as in the flowchart of FIG. 23. Optionally the receiving carer may generate and transmit a POLL request to the person cared for 3310. Also optionally the receiving carer may generate and transmit a CHECK request to a helper or a volunteer 3315.

If no responses are received within a time period, an ALARM REQUEST may be generated and transmitted to an alarm center 3320.

FIG. 34 shows an overview of a mobile communication terminal 620 (also referring to FIG. 6) to be used by a carer. The mobile communication terminal 620 is configured to display a graphical user interface comprising four virtual keys 34135. One virtual key is for accessing administrator settings, and one virtual key is for displaying information about the person cared for. Also shown are virtual keys for sending an "Are you ok?" request (SEND ARE YOU OK?) and a virtual key for accessing a log of events and conversations (EVENT AND CONVERSATIONS LOG), possibly including requests and confirmations, relating to the person cared for.

FIG. 35 shows an overview of a mobile communication terminal 610 (also referring to FIG. 6) to be used by a person cared for. The mobile communication terminal 610 is configured to display a graphical user interface comprising at least one virtual key 35135. The virtual key(s) is/are arranged to generate and transmit a request when they are activated or pressed. The type of the request is determined based on which virtual key 34135 is pressed. Alternatively, the mobile communication terminal 610 may also comprise physical keys (referenced 130 in FIG. 1) being associated with generating a request of a specific type. As a controller of the mobile communication terminal 610 receives an actuation of the key, the message or request is generated and associated with the message type being associated with the activated key. In the example of FIG. 35 four virtual keys are displayed 35135. One being for initiating a safety timer, and as it expires generate and transmit a safety timer request as has been disclosed above in relation to FIGS. 28 and 29; one being for generating and sending a contact request (REQUEST); one being for generating and transmitting a help request (HELP REQUEST) and one being for accessing a log of events and conversations possibly including requests and confirmations (EVENT AND CONVERSATIONS LOG).

Refined embodiments of a communication system for providing remote care taking of a first user, i.e. person, to be cared for by a plurality of second users will now be described with reference to the remaining FIGS. 36-40. The communication system may, for instance, be implemented by the communication system or telecare communication system according to any of the embodiments described with reference to the preceding figures.

The communication system for providing remote care taking of a first user to be cared for by a plurality of second users comprises a first mobile communication terminal which is configured for use by the first user to be cared for. The first mobile communication terminal may, for instance, be implemented by the mobile communication terminal 100, 200, 610 according to the preceding figures and may advantageously be a mobile phone.

The communication system also comprises a plurality of second mobile communication terminals for use by respective ones of the second users. Each second mobile communication terminal is configured to let the respective second user act as a member of a first recipient layer or a member of a second recipient layer. Each second mobile communication terminal may, for instance, be implemented by the mobile communication terminal 100, 200, 620 according to the preceding figures and may advantageously be a mobile phone.

The first mobile communication terminal 100, 200, 610 is configured to allow the first user to select a first element in a user interface of the first mobile communication terminal to cause sending of a first type of remote care taking request message intended for second users being members of the first recipient layer. The first type of request message pertains to remote care taking of the first user.

Advantageously, the second users which are members of the first recipient layer may be carers of the first user to be cared for, as has been described above for FIG. 24 and onwards. Hence, the first type of request message may be a contact request configured to trigger the second user of the receiving second mobile communication terminal 100, 200, 620 to initiate contact with the first user to be cared for. The selectable first element in the user interface of the first mobile communication terminal 100, 200, 610 can hence be a Contact Request button, as is seen in FIG. 35, or generally any kind of selectable UI element including, without limitation, buttons, menu options or gestures in a graphical UI, hard keys or other physical elements, speech recognition commands, etc. Carers are advantageously a small group comprising members of the first user's near family, such as the children of the first user. The first recipient layer can thus be seen as an Inner Circle layer around the first user.

The first mobile communication terminal 100, 200, 610 is moreover configured to allow the first user to select a second element in the user interface of the first mobile communication terminal to cause sending of a second type of request message intended for second users being members of the second recipient layer. The second type of request message also pertains to remote care taking of the first user but is different from the first type of request message.

Advantageously, the second users which are members of the second recipient layer may be helpers of the first user to be cared for, as has been described above for FIG. 24 and onwards. Hence, the second type of request message may be a help request configured to trigger the second user of the receiving second mobile communication terminal 100, 200, 620 to initiate an activity to help the first user to be cared for. The selectable second element in the user interface of the first mobile communication terminal 100, 200, 610 can hence be a Help Request button, as is seen in FIG. 35, or generally any kind of selectable UI element including, without limitation, buttons, menu options or gestures in a graphical UI, hard keys or other physical elements, speech recognition commands, etc. Helpers are advantageously family members of the first user, and/or relatives to the first user, and/or friends of the first user. The second recipient layer can thus be seen as a Friends & Family layer around the first user.

The first mobile communication terminal 100, 200, 610 may be configured to cause sending of the contact request only to second users being members of the first recipient layer (i.e. carers) but cause sending of the help request both to second users being members of the first recipient layer (i.e. carers) and to second users being members of the second recipient layer (i.e. helpers). This setup represents an intelligent trade-off between user integrity and security (the first user does not have to feel embarrassed by "disturbing" a large number of people with a contact request, but at the same time enjoy help from a large number of people whenever a situation arises where help is needed (a situation where the first user needs help being considered as more severe than a situation where the first user wishes contact).

When a second mobile communication terminal 100, 200, 620 has initiated contact with the first user to be cared for, or has initiated the activity to help the first user to be cared for, respectively, the communication system may be configured to cause notification to second users which are members of the same first or second recipient layer, respectively, as the initiating second mobile communication terminal. In this way, other members of the same recipient layer are automatically notified that another member of the same recipient layer has already attended to the contact request or help request, respectively.

In the communication system for providing remote care taking of the first user to be cared for by the plurality of second users, monitoring of the activity of the first user is preferably provided for. This monitoring may or may not be based on the functionality described above for FIGS. 32 and 33.

Figure 36:
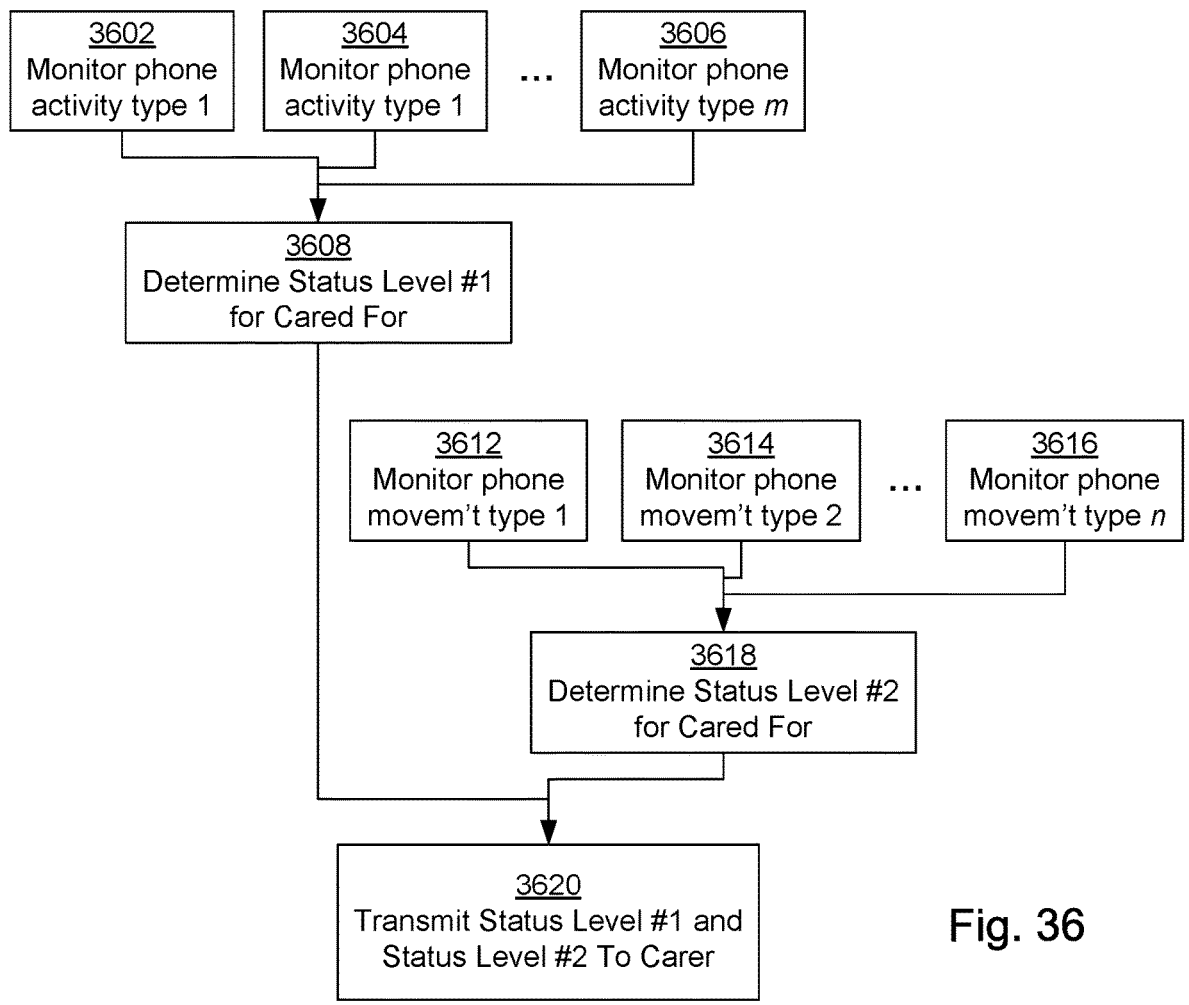
FIGS. 36-40 illustrate embodiments of a communication system for providing remote care taking of a first user to be cared for, including monitoring the activity of the user to be cared for, which are believed to be particularly advantageous.

The first mobile communication terminal 100, 200, 610 of the first user to be cared for is configured to perform the monitoring functionality illustrated in FIG. 36. The functionality illustrated in FIG. 36 may advantageously be performed by an application program installed in the first mobile communication terminal of the first user to be cared for.

As seen in FIG. 36, the first mobile communication terminal of the first user to be cared for monitors one or more types of activities performable by the first user to be cared for with the first mobile communication terminal. This is seen at 3602-3606. Examples of activity types are the answering of incoming phone calls, the generation of outgoing phone calls, the reading of incoming messages (such as SMS, MMS, email or chat messages), the generation of outgoing messages, the use of a certain application program such as a web browser, etc.

As seen at 3608, the first mobile communication terminal of the first user to be cared for determines a status level, Status Level #1, based on the monitoring of the types of activities at steps 3602, 3604, 3606. The Status Level #1 represents a degree of activity by the first user to be cared for. The Status Level #1 is then transmitted, as seen at 3620, to second users being members of the first recipient layer.

Advantageously, for refined accuracy, the first mobile communication terminal 100, 200, 610 is configured to monitor at least two different types of activities performable with the first mobile communication terminal by the first user to be cared for. In other words, at least two of the monitoring steps 3602-3606 are used. The Status Level #1 may then be determined by comparing the monitored types of activities to respective criteria for sufficient activity by the first user to be cared for.

A criterion for sufficient activity for a first type of activity may a first threshold number of occurrences of the first type of activity during a time period, and the criterion for sufficient activity for a second type of activity may be a second threshold number of occurrences of the second type of activity during the same or another time period. To account for the relative importance of the first and second types of activities, respectively, the first threshold number of occurrences may be different from the second threshold number of occurrences.

Advantageously, the first mobile communication terminal 100, 200, 610 is configured to set the Status Level #1 to represent sufficient activity by the first user to be cared for if at least one of the monitored first and second types of activities is found to satisfy its criterion. Alternatively or additionally, the first mobile communication terminal 100, 200, 610 may be configured to set the Status Level #1 to represent less than sufficient activity by the first user to be cared for if none the monitored first and second types of activities is found to satisfy its criterion.

If at least one the monitoring steps 3602-3606 indicates that sufficient activity has been performed during a period of time, this is an indication that the first user to be cared for is active and presumably being ok. Hence, Status Level #1 is set to a first value, which will represent a low alert need and may be represented, for instance, by a Green status in a traffic light notion. Sufficient activity may, for instance be the answering of at least one incoming phone call, or the reading of at least one incoming message, etc, during a given period of time, such as the duration of today's date.

As an alternative, Status Level #1 may be set to the first value, e.g. Green, by default, such as at the beginning of each day, or at power-up of the mobile communication terminal of the first user to be cared for.

If none of the monitoring steps 3602, 3604, 3606 indicates sufficient activity having been performed, then Status Level #1 will be set to a second value, which will represent a medium alert need and may be represented, for instance, by a Yellow status in a traffic light notion. Such insufficient activity may be the case when, for instance, the first user to be cared for has missed a first threshold number of incoming phone calls or has not read a second threshold number of incoming messages, wherein the first threshold number may be, for instance, one (1) missed incoming phone call and the second threshold number may be two (2) unread messages. The reason for having the first threshold number lower than the second threshold number may be to reflect that an incoming call is more likely to be noticed by the first user to be cared for than an incoming message; a missed call is therefore a clearer indication of something possibly being wrong with the first user to be cared for, than an unread message. In alternative embodiments, however, the first and second threshold numbers may have the same value.

If the monitoring steps 3602, 3604, 3606 indicate that the insufficient activity prevails for more than a threshold time, such as for instance a duration xx:yy hours:minutes since the Status Level #1 was set to the second value (e.g. Yellow), then the Status Level #1 will be set to a third value, which will represent a high alert need and may be represented, for instance, by a Red status in a traffic light notion.

Likewise, if the monitoring steps 3602, 3604, 3606 indicate that the insufficiency of activity is worsened (i.e. any of the monitored types of activities is found to indicate increased inactivity by the first user to be cared for), the Status Level #1 may be set to the third value (e.g. Red). This may for instance be the case when the missed incoming calls exceed a third threshold number, higher than the first threshold number, such as two (2) missed incoming phone calls, or when the unread messages exceed a fourth threshold number, higher than the third threshold number, such as four (4) unread messages.

In addition to the monitoring of the activity types in steps 3602, 3604 and 3606, and the determination of the Status Level #1 accordingly in step 3608, the first mobile communication terminal of the first user to be cared for may—optionally but advantageously—also be configured to monitor one or more types of movements of the first mobile communication terminal 100, 200, 610 of the first user to be cared for. This is seen at 3612, 3614 and 3616 in FIG. 36. To measure movement of the first mobile communication terminal 100, 200, 610, the first mobile communication terminal may use any available resources, such as one or more accelerometers, a satellite positioning signal receiver, etc, or any combination thereof.

In this embodiment, the first mobile communication terminal 100, 200, 610 is further configured to, based on the monitoring step(s) 3612-3616, determine (step 3618) a second status level Status Level #2 (wherein the aforementioned Status Level #1 will be the first status level). Status Level #2 will represent a degree of movement of the first mobile communication terminal 100, 200, 610. In this embodiment, the first mobile communication terminal 100, 200, 610 is moreover configured to transmit (step 3620) the first as well as second status levels Status Level #1, Status Level #2 to second users being members of the first recipient layer.

The first mobile communication terminal 100, 200, 610 may be configured to monitor, 3612-3616, at least two different types of movements of the first mobile communication terminal, and to determine, 3618, Status Level #2 by comparing the monitored types of movements to respective criteria.

A first movement type may, for instance, be a movement exceeding a certain distance, whereas a second movement type may be, for instance, a movement lasting more for more than a threshold time duration, such as xx seconds. A third movement type may be a movement to a certain position or area of positions, whereas a fourth movement type may be a movement from a certain position or area of positions.

As seen at 3618, the first mobile communication terminal of the first user to be cared for determines a Status Level #2 based on the monitoring of the types of movements at steps 3612, 3614, 3616. If at least one the monitoring steps 3612, 3614, 3616 indicates that the first mobile communication terminal of the first user to be cared for has been moved, this is an indication of sufficient movement of the first mobile communication terminal and implicitly that the first user to be cared for is active and presumably being ok. Hence, Status Level #2 is set to a first value, which (like Status Level #1) will represent a low alert need and may be represented, for instance, by a Green status in a traffic light notion. For improved accuracy, step 3618 may require concurrent movement indications from two of the monitoring steps 3612, 3614, 3616 in order to determine that Status Level #2 shall be set to the first value, e.g. Green. This will avoid a spurious detection by one of the monitoring steps 3612, 3614, 3616 from being considered as a "valid" movement of the mobile communication terminal by an active and well-being first user to be cared for.

If, on the other hand, it is concluded in step 3618 that none of the monitoring steps 3612, 3614, 3616 has indicated a movement of the first mobile communication terminal of the first user to be cared for during a first threshold duration time, such as x hours, then Status Level #2 will be set to a second value to represent less than sufficient movement of the first mobile communication terminal. The second value may (as for Status Level #1) represent a medium alert need and may be represented, for instance, by a Yellow status in a traffic light notion.

Then, if it is concluded in step 3618 that none of the monitoring steps 3612, 3614, 3616 has indicated a movement of the first mobile communication terminal of the first user to be cared for during a second threshold duration time, such as y hours, where y>x, then Status Level #2 will be set to a third value, which (as for Status Level #1) will represent a high alert need and may be represented, for instance, by a Red status in a traffic light notion. The third value (RED) may thus be set when the second status level has represented less than sufficient movement during a threshold time period, or when any of the monitored types of movements is found to imply increased inactivity by the first user to be cared for (e.g. when the monitored movement is further decreased or ceases completely).

While monitoring of several different movement types will generally increase the accuracy in the monitoring functionality, it may also suffice to monitor for just a single movement type (i.e., step 3612 alone). Such a single movement type will then preferably represent any type of movement, in any direction, amount or duration, possibly subject to a certain minimum threshold value.

As is apparent from the description above, two independent indications of the well-being of the first user to be cared for may advantageously be produced by the step 3608 in the form of Status Level #1 (being based on a detected inactivity of the first user to be cared for in using the first mobile communication terminal), and by the step 3618 in the form of Status Level #2 (being based on a detected non-movement of the first mobile communication terminal by the first user to be cared for). This increases the reliability of the monitoring functionality.

In step 3620 in FIG. 36, the first mobile communication terminal 100, 200, 610 of the first user to be cared for transmits the value of Status Level #1, and when applicable also the value of Status Level #2, to second users being members of the first recipient layer, e.g. to the or each carer of the first user to be cared for. As has been described previously in this document, the transmission may handled by a message handler, such as the server 650 in FIG. 6. By only transmitting the value of Status Level #1 (and when applicable Status Level #2), no personal details of the first user to be cared for, such as pictures, moving images, behavior patterns, etc, have to be recorded or transmitted. Hence, an advantage in personal integrity preservation is obtained, as well as in a reduced need for data storage in or for the first mobile communication terminal 100, 200, 610.

The functionality on the receiving side, i.e. functionality which may occur for each second mobile communication terminal 100, 200, 620 which is configured to let the respective second user act as a member of the first recipient layer, will now be described. The second mobile communication terminal 100, 200, 620 is configured to receive the Status Level #1 (and when applicable Status Level #2) from the first mobile communication terminal 100, 200, 610, and to provide a first indication of the received Status Level #1 (and when applicable a second indication of the received Status Level #2) to the second user in a user interface of the second mobile communication terminal 100, 200, 620.

Figure 37:
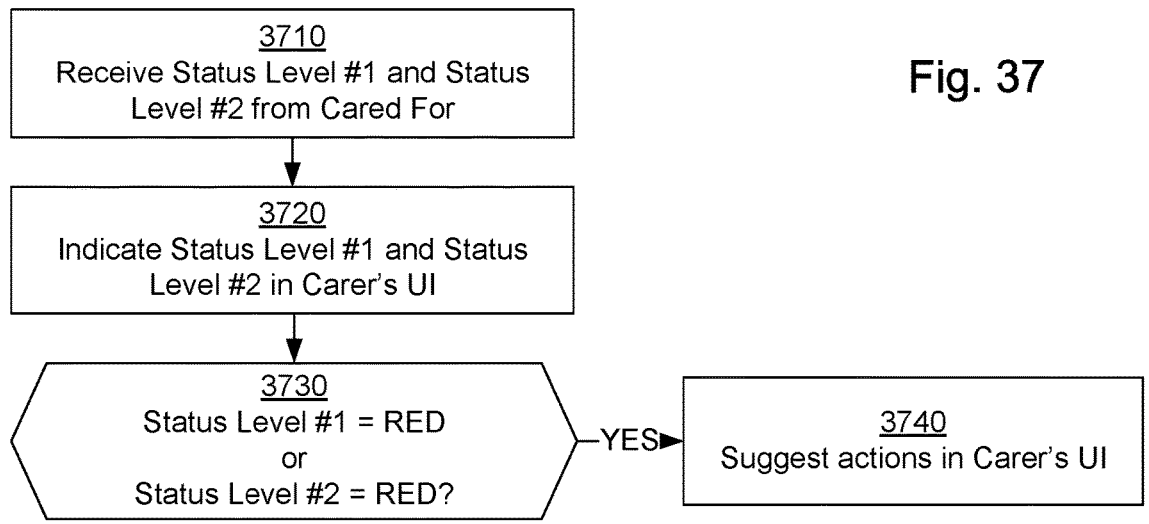

FIG. 37 thus illustrates the functionality performed by the second mobile communication terminal of, for instance, a carer in an embodiment which matches FIG. 36. The carer's second mobile communication terminal may for instance be any of the terminals 100, 200 or 620 as referred to previously in this document, and may advantageously be a mobile phone. The functionality illustrated in FIG. 37 may advantageously be performed by an application program installed in the second mobile communication terminal of each carer.

In step 3710, the second mobile communication terminal 100, 200, 620 of the carer receives the values of Status Level #1 and Status Level #2 as produced and transmitted by the first mobile communication terminal of the first user to be cared for. Then, in a step 3720, the received values of Status Level #1 and Status Level #2 are indicated in the user interface of the carer's mobile communication terminal.

Figure 38:
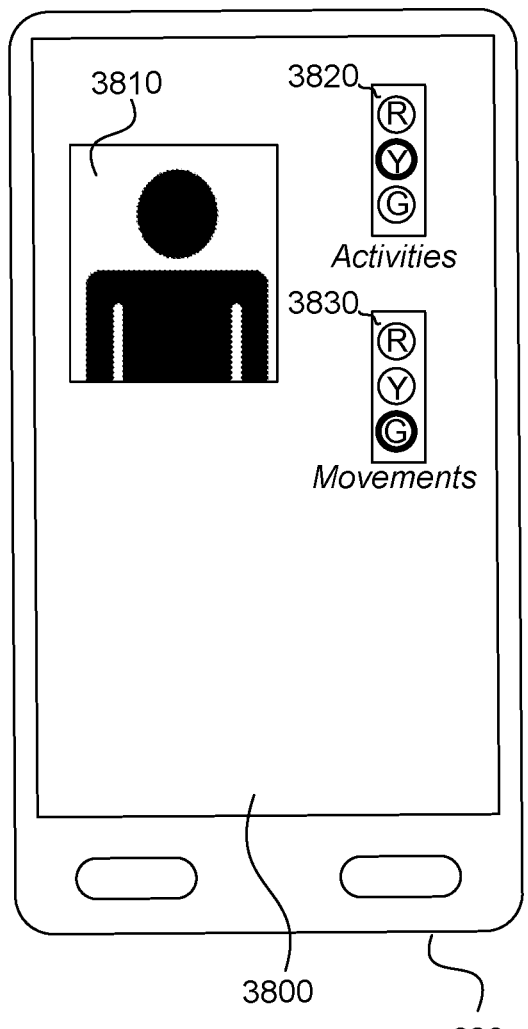

As is seen in FIG. 38, the indication of the received value of Status Level #1 may advantageously be made in the form of a first traffic stoplight notion 3820 on the display screen 3800 of the carer's second mobile communication terminal 620. If Status Level #1, for instance, has the second value which represents the medium alert need, the yellow lamp in the traffic stoplight notion 3820 is lit, highlighted or otherwise marked (in FIG. 38 this is illustrated by a thick circle around "Y").

Correspondingly, as is seen in FIG. 38, the indication of the received value of Status Level #2 may advantageously be made in the form of a second traffic stoplight notion 3830 on the display screen 3800 of the carer's second mobile communication terminal 620. In FIG. 38, the second traffic stoplight notion 3830 has the green lamp lit, highlighted or otherwise marked; hence, the received value of Status Level #2 is the first value which represents the low alert need.

As is seen in FIG. 38, a still picture 3810 of the first user to be cared for may be presented on the display screen 3800 of the carer's second mobile communication terminal 620. Hence, the carer will be given very intuitive information about the current well-being of the first user to be cared for, simply by making a quick glimpse at the first and/or second traffic stoplight notions 3820, 3830. If both of them indicates green, the carer may rest assured that the first user to be cared for is well for the time being.

If, on the other hand, at least one of the traffic stoplight notions 3820, 3830 shows a yellow, or, even worse, a red light, then the carer may immediately conclude that some action should be taken with respect to the first user to be cared for in any of the ways offered and described in other sections of this document.

Should both of the traffic stoplight notions 3820, 3830 show a yellow, or, even worse, a red light, then the carer may be even more convinced that action must be taken.

To facilitate even further for the carer, the carer's second mobile communication terminal 620 may determine, in a step 3730 in FIG. 37, whether at least one of Status Level #1 and Status Level #2 has a value which represents the high alert need, e.g. Red. If so, the carer's second mobile communication terminal 620 may proceed to a step 3740 in which UI elements representing suggested actions are automatically provided in the user interface of the carer's mobile communication terminal.

Figure 39:
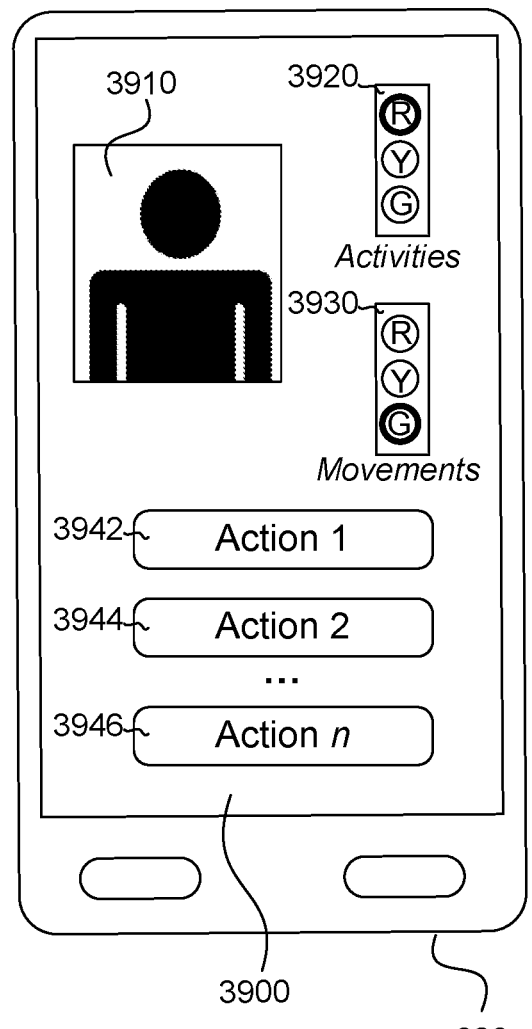

A first example of this can be seen in FIG. 39, where a first UI element representing a first suggested action is provided in the form of a first virtual button 3942 (or other selectable user interface item) below the picture 3910 of the first user to be cared for and the first and second traffic stoplight notions 3920, 3930 on the display screen 3900 of the carer's second mobile communication terminal 620. Correspondingly, further virtual buttons 3944, 3946, . . . , may offer further suggested actions. Examples of suggested actions may, for instance, be Call the first user to be cared for, Send message to the first user to be cared for, Send Are You OK message, Generate alarm, etc.

Figure 40:
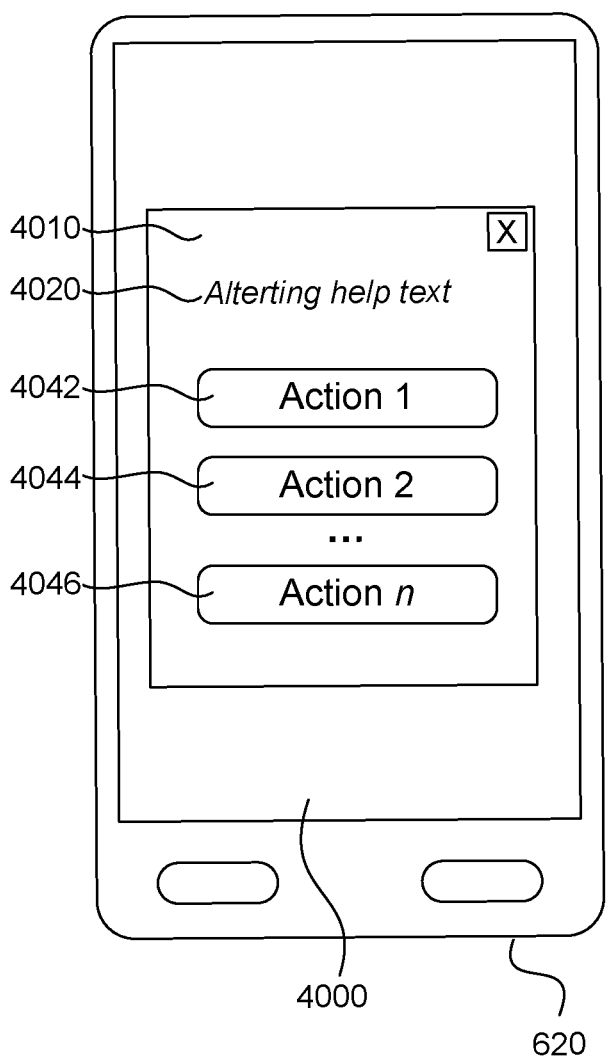

As an alternative, as seen in FIG. 40, the UI elements representing suggested actions may be provided as virtual buttons 4042, 4044, 4046, . . . (or other selectable user interface items) in a separate pop-up window or alert box 4010, together with an alerting help text 4020, on the display screen 4000 of the carer's second mobile communication terminal 620.

The carer's second mobile communication terminal 620 is further configured to detect a selection of the or one of the elements; and cause performance of the action represented by the selected element. As already indicated, this may for instance involve placing a telephone call to the first mobile communication terminal 100, 200, 610, sending a message to the first user to be cared for, or generating an alarm to an alarm service provider.

The functionality at the first mobile communication terminal 610 of the first user to be cared for according to FIG. 36 may advantageously be performed constantly or at least according to a predefined scheme, i.e. at regular intervals, to allow the carer's second mobile communication terminal to receive current values of Status Level #1 and Status Level #2 and keep the user interface updated.

The reference data required for the monitoring of activity and phone movements according to the functionality shown in FIG. 36 may for instance be set upon installation of the aforementioned application program in the first mobile communication terminal of the first user to be cared for. The installer, which typically may be one of the carers, may appropriately configure the reference data to suit the expected behaviour patterns of the first user to be cared for. Examples of reference data are: which activity types to monitor, the number of activity types to monitor, which movement types to monitor, the number of movement types to monitor, the various threshold time periods for the monitoring, and the various threshold numbers for the monitoring.

Alternatively, the aforementioned application program in the first mobile communication terminal may be configured to automatically detect the general behavior patterns of the first user to be cared for during an initial period of use of the application program, and automatically configure the reference data to suit the detected behaviour patterns of the first user to be cared for.

Updates to the reference data may also be made over time, either manually or automatically, to adjust for long-term changes in the behavior patterns of the first user to be cared for because of ageing, decreasing physical capability, decreasing mental capability—or, on the other hand, growing experience or appetite of using the first mobile communication terminal.

Refined embodiments of handling of assistance upon request from the first user to be cared for, which is enabled by a communication system according to the teachings herein and which may or may not be based on the assistance handling functionality described above for FIGS. 24 and 26, will now be described.

Generally, for these refined embodiments, each second mobile communication terminal 100, 200, 620 is configured to let the respective second user act as a member of the first recipient layer, a member of the second recipient layer or a member of a third recipient layer, wherein the third recipient layer represents second users being volunteers to provide assistance to the first user to be cared for. The first mobile communication terminal 100, 200, 610 is configured to allow the first user to select a third element in a user interface of the first mobile communication terminal to cause sending of a third type of request message intended for second users, the third type of request message being an assistance request configured to urge the second user of a receiving second mobile communication terminal to provide assistance to the first user to be cared for.

Generally, for these refined embodiments, the communication system may be further configured to send the assistance request to second users being members of at least either the first or second recipient layer, detect that no such second user has accepted the assistance request during a threshold time period, and forward the assistance request to second users being members of the third recipient layer. This represents an intelligent trade-off between personal integrity and security of the first user, since assistance requests are first only sent to the first and/or second layers, the members of which are known to the first user. Only if none of them is able to attend to the assistance request, will the assistance request be sent to a larger group of volunteers, the identities of which will typically not be known to the first user, but the number of which may be large enough to guarantee, at a sufficient likelihood, that one of them will be able to provide the requested assistance.

Generally, for these refined embodiments, the communication system may be further configured to detect that a second user has accepted the assistance request, and cause notification to the first user to be cared for as well as to second users being members of at least either the first or second recipient layer.

Generally, for these refined embodiments, the first mobile communication terminal 100, 200, 610 may be configured to receive an offer from a second user being a member of the third recipient layer to attend to the assistance request, provide an element in the user interface of the first mobile communication terminal to accept or decline the offer, detect a selection of the element by the first user to be cared for, and if the selection indicates acceptance of the offer, accordingly notify the second user being a member of the third recipient layer. This will give the first user control over whether or not to accept assistance from a certain second user.

Alternatively or additionally, the first mobile communication terminal 100, 200, 610 may be configured to receive an offer from a second user being a member of the third recipient layer to attend to the assistance request, provide an element in the user interface of the first mobile communication terminal to accept or decline the offer, detect that the first user to be cared for has not actively declined the offer during a threshold time period, and automatically notify the second user being a member of the third recipient layer that the offer has been accepted. This will improve security, since the offer to assist will be automatically accepted in case of an omitted reaction from the first user—whose critical situation may have become worse since the assistance request was made, thereby incapacitating him or her and preventing due acceptance of the offer to assist.

A request for assistance can be made by the first user to be cared for from his mobile communication terminal, for instance by pressing a physical assistance key on the mobile communication terminal, or selecting a virtual assistance button in the user interface of the mobile communication terminal. Since a request for assistance will typically be made when the first user to be cared for experiences a potentially hazardous situation, the assistance request is preferably sent not only to the carers but also to the helpers. In addition, volunteers are preferably used as back-up in case no helpers are available to assist the first user to be cared for.

Therefore, an application program is installed in the first mobile communication terminal of the first user to be cared for to handle a first side of the assistance handling functionality, as seen from the point of view of the first user to be cared for. Moreover, an application program is installed in the second mobile communication terminal of each carer and each helper to handle a second side of the assistance handling functionality, as seen from the point of view of the carer or helper. Additionally and preferably, an application program is installed in the second mobile communication terminal of each volunteer to handle a third side of the assistance handling functionality, as seen from the point of view of the volunteer.

The functionality flow for the handling of an assistance request in one embodiment will now be described.

When the first user to be cared for has made the request for assistance, he may be provided with an opportunity to cancel his request within a short period of time, such as x seconds. To this end, information may be provided in the user interface of the mobile communication terminal of the first user to be cared for to inform him that a) the assistance button or key has been activated, and b) than he may cancel the request and avoid the sending of the assistance request within x-n seconds, where n is the number of seconds lapsed since the assistance button or key was activated.

The assistance request is then sent to the helpers in the system. The carers may typically be included as a subgroup of the helpers. Feedback is given to the first user to be cared for in the user interface of his mobile communication terminal to inform him that the assistance request has been sent to the helpers. The first user to be cared for may also be given an update on the progress of the handling of the assistance request; the user interface of the mobile communication terminal of the first user to be cared for may provide information to indicate when any of the helpers have accepted the assistance request. Also, the user interface of the mobile communication terminal of the first user to be cared for may provide information that the assistance request will be forwarded to volunteers if no helper accepts the assistance request within a threshold time period of, e.g., y minutes. The first user to be cared for may also be given an option to prevent such forwarding of a non-accepted assistance request to volunteers, and an option to cancel the assistance request.

On the helper side, information may be provided in the user interface of the mobile communication terminal of each helper that the first user to be cared for has issued an assistance request. At the same time, the helper may be provided with an option, for instance in the form of a virtual button in the user interface, to accept the assistance request. When one helper accepts the assistance request, this information will be fed back to the first user to be cared for and also to other helpers in the system.

The helper may also be provided with an option to respond to the assistance request by way of another action, such as initiating a telephone call to the first user to be cared for.

Finally, particularly if the helper is a carer, or possibly for any helper, the helper may also be provided with an option to forward the assistance request to the volunteers (unless the first user to be cared for has prohibited such forwarding, as described above). Forwarding of an assistance request may be made to all volunteers in the system, but in an advantageous embodiment, the assistance request is forwarded only to a subgroup of all volunteers, typically volunteers which are geographically close to the first user to be cared for.

The system may also have functionality to automatically forward an assistance request to volunteers, if it has been found that no helper has accepted the assistance request during a threshold time period, such as x minutes, as counted from the time when the assistance request was sent from the first mobile communication terminal of the first user to be cared for.

When a mobile communication terminal of a volunteer receives a forwarded assistance request, it will provide information to this effect in the user interface of the volunteer's mobile communication terminal. This information may include certain, limited information about the first user to be cared for, such as his approximate geographical position, or his relative distance to the volunteer. The information may also include an option for the volunteer to submit his offer to attend to the assistance request. Moreover, the information may also include an option for the volunteer to submit a statement that he is not available to assist with this request.

If a volunteer decides to respond to an assistance request, certain handshaking between the mobile communication terminals is preferably made. On the mobile communication terminal of the first user to be cared for, information may be provided to inform the first user to be cared for about the volunteer's offer to attend to the assistance request. The information may include an option for the first user to be cared for to accept the offer, or to decline the offer.

If the first user to be cared for chooses to decline the offer, the volunteer will be informed in the user interface of his mobile communication terminal that his assistance is not needed this time, with thanks.

If the first user to be cared for chooses to accept the offer, the volunteer will be informed accordingly in the user interface of his mobile communication terminal. Advantageously, the volunteer may also be given more detailed information about the first user to be cared for at this stage, such as his exact whereabouts, or a direct communication channel in the form of, for instance, a chat log. Hence, information which may be sensitive in terms of personal integrity is only communicated once the first user to be cared for has accepted the offer.

For safety reasons, the mobile communication terminal of the first user to be cared for may be configured to automatically accept an offer to assist from a volunteer, if the first user to be cared for has not actively declined it within a certain threshold time period. This is a fail-safe provision which will enable assistance in a situation where the first user to be cared for becomes incapacitated, e.g. unconscious or severely worse, shortly after having activated the assistance key or button.

Moreover, in some implementations a carer included among the helpers, or possibly any helper, may accept an offer to assist from a volunteer on behalf of the first user to be cared for.

The volunteers in the system may be physical persons acting as individuals, but one or more of them may optionally be associated with an alarm central, telecare central, guard service, emergency service, etc.

When a volunteer has offered to attend to an assistance request, and the offer has been accepted (manually or automatically in any of the ways referred to above), this information may also be distributed to the helpers, preferably by identifying the volunteer, and to other volunteers that offered to attend but the offers of which were not accepted, preferably by a message stating that the kind offer to assist has been noticed with thanks but will not be needed this time.

The teachings herein have mainly been described above with reference to a few embodiments. However, as is readily appreciated by a person skilled in the art, other embodiments than the ones disclosed above are equally possible within the scope of the invention, as defined by the appended patent claims.

Other inventive aspects of the present disclosure are defined by the following numbered clauses.

I. A communication apparatus 100, 200, 3000, 400, 610, 650 comprising a controller 210, wherein said controller 210 is configured to:
receive a message, such as a communication request;
determine a type for said message;
select a first recipient layer based on said type, said first recipient layer comprising at least one recipient; and
transmit said message to at least one of said at least one recipient of said first recipient layer.

II. The communication apparatus 100, 200, 3000, 400, 610, 650 of clause I, wherein said controller 210 is further configured to:
receive a confirmation from said at least one of said at least one recipient of said first recipient layer; and in response thereto
transmit said confirmation from said at least one of said at least one recipient of said first recipient layer to at least another one of said at least one recipient of said first recipient layer.

III. The communication apparatus 100, 200, 3000, 400, 610, 650 according to clause II, wherein said controller 210 is further configured to select a second recipient layer, said second recipient layer comprising at least one recipient and being a higher recipient layer than said first recipient layer, and to
transmit said confirmation from said at least one of said at least one recipient of said first recipient layer to at least one of said at least one recipient of said second recipient layer.

IV. The communication apparatus 100, 200, 3000, 400, 610, 650 according to clause II or III, wherein said controller 210 is further configured to
determine that no confirmation has been received, and in response thereto
retransmit said message to said at least one of said at least one recipient of said first recipient layer; and/or transmit a reminder of said message to said at least one of said at least one recipient of said first recipient layer.

V. The communication apparatus 100, 200, 3000, 400, 610, 650 according to clause IV, wherein said controller 210 is further configured to select a third recipient layer, said third recipient layer comprising at least one recipient and being a lower recipient layer than said first recipient layer, and to retransmit said message to at least one of said at least one recipient of said third recipient layer; and/or transmit a reminder of said message to at least one of said at least one recipient of said third recipient layer.

VI. The communication apparatus 100, 200, 3000, 400, 610, 650 according to any preceding clause, wherein said message comprises data and said controller 210 is further configured to filter said data based on said message type before transmitting said message to at least one of said at least one recipient of said first recipient layer.

VII. The communication apparatus 100, 200, 3000, 400, 610, 650 according to any preceding clause, wherein said controller 210 is further configured to receive a selected forwarding layer, being a fourth recipient layer comprising at least one recipient and transmit said message to at least one of said at least one recipient of said fourth recipient layer.

VIII. The communication apparatus 100, 200, 3000, 400, 610, 650 according to any preceding clause, wherein said controller 210 is further configured to:
identify a sender of said message;
receive a position of said sender;
receive at least one position of said at least one recipient of said first recipient layer;
determine a distance between said sender and said at least one recipient of said first recipient layer; and
based on said distance, select said at least one of said at least one recipient of said first recipient layer to transmit said message to.

IX. A method for use in a communication apparatus 100, 200, 300, 400, 610, 650, wherein said method comprises
receiving a message, such as a communication request;
determining a type for said message;
selecting a first recipient layer based on said type, said first recipient layer comprising at least one recipient; and
transmitting said message to at least one of said at least one recipient of said first recipient layer.

X. A mobile communications terminal 200, 620 being associated with a first recipient layer and comprising a controller 210, wherein said controller 210 is configured to
receive a message, such as a communication request, wherein said message is associated with said first recipient layer.

XI. The mobile communications terminal 200, 620 according to clause X, wherein said controller 210 is further configured to:
select a forwarding recipient layer; and
cause said received message to be transmitted to at least one of at least one recipient of said forwarding recipient layer.

XII. The mobile communications terminal 200, 620 according to clause X or XI, wherein said controller 210 is further configured to send an alarm request in response to receiving said message.

XIII. The mobile communications terminal 200, 620 according to any of clauses X to XII, wherein said controller 210 is further configured to:
generate a message, said message being associated with an are you ok type (ARE YOU OK?);
transmit said message to a mobile communication terminal 610 belonging to a person cared for;
determine that no response to said message is received; and, in response thereto;
generate and transmit an alarm request.

XIV. The mobile communications terminal 200, 620 according to any of clauses X to XIII, wherein said controller 210 is further configured to:

receive a message indicating an activity of a person cared for; and in response thereto,
generate and transmit a polling message to said person cared for requesting further details, and/or
generate and transmit a check request to be transmitted to a second recipient layer, and/or
generate and transmit an alarm request.

XV. A mobile communications terminal 200, 610 comprising a controller 210, wherein said controller 210 is configured to
generate a message, such as a communication request, and associate said message with a type.

XVI. The mobile communications terminal 200, 610 according to clause XV, wherein said mobile communications terminal 200, 610 is a communications apparatus according to any of clauses I to IX.

XVII. The mobile communications terminal 200, 610 according to clause XV or XVI, wherein said controller 210 is further configured to determine that a safety timer has expired and in response thereto generate said message and associate said message with a type being a safety timer request.

XVIII. The mobile communications terminal 200, 610 according to any of clauses XV to XVII, wherein said controller 210 is further configured to
monitor an activity;
generate said message as an activity request based on said monitored activity.

XIX. The mobile communications terminal 200, 610 according to clause XVIII, wherein said activity relates to one or more of an activity taken from a group comprising: placement and acceptance of voice or video calls; sending and opening of messages; use of an application; movement of a mobile communication terminal belonging to a person cared for; network status of the mobile communication terminal belonging to the person cared for.

XX. The mobile communications terminal 200, 610 according to any of clauses XV to XIX, further comprising a key 130, 135, 35135, wherein said controller 210 is further configured to:
associate said key 130, 135, 35135 with a message type; and
receive an actuation of said key 130, 135, 35135 and in response thereto generate said message, wherein said message type is the message type associated with the key 130, 135, 35135.

XXI. A communications system 600 comprising a communication apparatus 100, 200, 300, 400, 610, 650, a first mobile communication terminal 100, 200, 610 and a second mobile communication terminal 100, 200, 620, wherein said first mobile communication terminal 100, 200, 610 possibly comprises said communication apparatus 100, 200, 3000, 400, 610, 650, wherein
said first mobile communication terminal 100, 200, 610 is configured to generate a message, such as a communication request, and associate said message with a type, wherein
said communication apparatus 100, 200, 300, 400, 610, 650 is configured to:
receive a message, such as a communication request;
determine a type for said message;
select a first recipient layer based on said type; and
transmit said message to at least said second mobile communication terminal (100, 200, 620), and wherein
said second mobile communication terminal 100, 200, 620 is associated with said first recipient layer and configured to receive said message.

XXII. A computer-readable storage medium 70 encoded with instructions 71 that, when executed on a processor, perform the method according to clause IX.

The invention claimed is:

1. A communication apparatus comprising a controller, wherein said controller is configured to:
receive a message, in a form of a communication request;
determine a type for said message;
select a first recipient layer based on said type, said first recipient layer comprising at least one recipient;
transmit said message to at least one of said at least one recipient of said first recipient layer;
receive a confirmation from said at least one of said at least one recipient of said first recipient layer; and in response thereto
transmit said confirmation from said at least one of said at least one recipient of said first recipient layer to at least another one recipient of said at least one recipient of said first recipient layer.

2. The communication apparatus according to claim 1, wherein said controller is further configured to select a second recipient layer, said second recipient layer comprising at least one recipient and being a higher recipient layer than said first recipient layer, and to
transmit said confirmation from said at least one of said at least one recipient of said first recipient layer to at least one of said at least one recipient of said second recipient layer.

3. The communication apparatus according to claim 2, wherein said controller is further configured to
determine that no confirmation has been received, and in response thereto
retransmit said message to said at least one of said at least one recipient of said first recipient layer; and/or transmit a reminder of said message to said at least one of said at least one recipient of said first recipient layer.

4. The communication apparatus according to claim 3, wherein said controller is further configured to select a third recipient layer, said third recipient layer comprising at least one recipient and being a lower recipient layer than said first recipient layer, and to retransmit said message to at least one of said at least one recipient of said third recipient layer; and/or transmit a reminder of said message to at least one of said at least one recipient of said third recipient layer.

5. The communication apparatus according to claim 4, wherein said controller is further configured to receive a selected forwarding layer, being a fourth recipient layer comprising at least one recipient and transmit said message to at least one of said at least one recipient of said fourth recipient layer.

6. The communication apparatus according to claim 1, wherein said message comprises data and said controller is further configured to filter said data based on said message type before transmitting said message to at least one of said at least one recipient of said first recipient layer.

7. The communication apparatus according to claim 1, wherein said controller is further configured to:
identify a sender of said message;
receive a position of said sender;
receive at least one position of said at least one recipient of said first recipient layer;
determine a distance between said sender and said at least one recipient of said first recipient layer; and
based on said distance, select said at least one of said at least one recipient of said first recipient layer to transmit said message to.

8. A method for use in a communication apparatus, wherein said method comprises;
- receiving a message, in a form of a communication request;
- determining a type for said message;
- selecting a first recipient layer based on said type, said first recipient layer comprising at least one recipient;
- transmitting said message to at least one of said at least one recipient of said first recipient layer;
- receiving a confirmation from said at least one of said at least one recipient of said first recipient layer; and in response thereto
- transmitting said confirmation from said at least one of said at least one recipient of said first recipient layer to at least another one recipient of said at least one recipient of said first recipient layer.

9. A communications system comprising a communication apparatus according to claim 8, a first mobile communication terminal and a second mobile communication terminal,
- wherein said first mobile communication terminal is configured to generate a message and associate said message with a type, and
- wherein said second mobile communication terminal is associated with said first recipient layer and configured to receive said message.

10. The communications system according to claim 9, wherein said first mobile communication terminal is further configured to determine that a safety timer has expired and in response thereto generate said message and associate said message with a type being a safety timer request.

11. The communications system according to claim 9, wherein said first mobile communication terminal is further configured to
- monitor an activity; and
- generate said message as an activity request based on said monitored activity.

12. The communications system according to claim 11, wherein said activity relates to one or more of an activity taken from a group consisting of:
- placement and acceptance of voice or video calls;
- sending and opening of messages;
- use of an application;
- movement of a mobile communication terminal belonging to a person cared for; and
- network status of the mobile communication terminal belonging to the person cared for.

13. The communications system according to claim 9, further comprising a key, wherein said first mobile communication terminal is further configured to:
- associate said key with a message type; and
- receive an actuation of said key and in response thereto generate said message, wherein the type of said generated message is the message type associated with the key.

14. A communication apparatus comprising a controller, wherein said controller is configured to:
- receive a message in a form of a communication request;
- determine a type for said message;
- in a recipient layer hierarchy in which a higher recipient layer is a layer with recipients having a higher priority or clearance or a stronger association with a message sender, and a lower recipient layer is a layer with recipients having a lower priority or clearance or a weaker if any association with the message sender, select a first recipient layer based on said type, said first recipient layer comprising at least two recipients;
- transmit said message to at least one of said at least two recipients of said first recipient layer;
- receive a confirmation from said at least one of said at least two recipients of said first recipient layer; and in response thereto
- transmit said confirmation received from said at least one of said at least two recipients of said first recipient layer to at least another one recipient of said at least two recipients of said first recipient layer,
- wherein said controller is further configured to:
  - select a second recipient layer, said second recipient layer comprising at least one recipient and being a higher recipient layer than said first recipient layer, and to
  - transmit said confirmation from said at least one of said at least two recipients of said first recipient layer to at least one of said at least one recipient of said second recipient layer,
  - and wherein recipients of a highest recipient layer are informed of a status or progress of all communication requests by receiving every communication request and also receiving every confirmation.

15. The communication apparatus according to claim 14, wherein said controller is further configured to
- determine that no confirmation has been received, and in response thereto
- retransmit said message to said at least one of said at least two recipients of said first recipient layer; and/or transmit a reminder of said message to said at least one of said at least one recipient of said first recipient layer.

16. The communication apparatus according to claim 15, wherein said controller is further configured to select a third recipient layer, said third recipient layer comprising at least one recipient and being a lower recipient layer than said first recipient layer, and to retransmit said message to at least one of said at least one recipient of said third recipient layer; and/or transmit a reminder of said message to at least one of said at least one recipient of said third recipient layer.

17. The communication apparatus according to claim 16, wherein said controller is further configured to receive a selected forwarding layer, being a fourth recipient layer comprising at least one recipient and transmit said message to at least one of said at least one recipient of said fourth recipient layer.

18. The communication apparatus according to claim 14, wherein said message comprises data and said controller is further configured to filter said data based on said message type before transmitting said message to at least one of said at least two recipients of said first recipient layer.

19. The communication apparatus according to claim 14, wherein said controller is further configured to:
- identify a sender of said message;
- receive a position of said sender;
- receive at least one position of at least one recipient of said first recipient layer;
- determine a distance between said sender and said at least one recipient of said first recipient layer; and
- based on said distance, select said at least one of said at least one recipient of said first recipient layer to transmit said message to.

20. A communications system comprising a communication apparatus according to claim 14, a first mobile communication terminal and a second mobile communication terminal, wherein
- said first mobile communication terminal is configured to generate a message in the form of a communication request, and associate said message with a type, and wherein said second mobile communication terminal is associated with said first recipient layer and configured to receive said message.

21. The communications system according to claim 20, wherein said first mobile communication terminal is further configured to determine that a safety timer has expired and in response thereto generate said message and associate said message with a type being a safety timer request.

22. The communications system according to claim 20, wherein said first mobile communication terminal is further configured to
    monitor an activity; and
    generate said message as an activity request based on said monitored activity.

23. The communications system according to claim 22, wherein said activity relates to one or more of an activity taken from a group comprising:
    placement and acceptance of voice or video calls;
    sending and opening of messages; use of an application;
    movement of a mobile communication terminal belonging to a person cared for; and
    network status of the mobile communication terminal belonging to the person cared for.

24. The communications system according to claim 20, further comprising a key, wherein said first mobile communication terminal is further configured to:
    associate said key with a message type; and
    receive an actuation of said key and in response thereto generate said message, wherein the type of said generated message is the message type associated with the key.

25. A method for use in a communication apparatus, wherein said method comprises:
    receiving a message in a form of a communication request;
    determining a type for said message;
    in a recipient layer hierarchy in which a higher recipient layer is a layer having recipients with a higher priority or clearance or a stronger association with a message sender, and a lower recipient layer is a layer with recipients having a lower priority or clearance or a weaker if any association with the message sender, selecting a first recipient layer based on said type, said first recipient layer comprising at least two recipients;
    transmitting said message to at least one of said at least two recipients of said first recipient layer;
    receiving a confirmation from said at least one of said at least two recipients of said first recipient layer; in response thereto
    transmitting said received confirmation from said at least one of said at least two recipients of said first recipient layer to at least another one recipient of said at least two recipients of said first recipient layer;
    selecting a second recipient layer, said second recipient layer comprising at least one recipient and being a higher recipient layer than said first recipient layer; and
    transmitting said confirmation from said at least one of said at least two recipients of said first recipient layer to at least one of said at least one recipient of said second recipient layer,
    wherein recipients of a highest recipient layer are informed of a status or progress of all communication requests by receiving every communication request and also receiving every confirmation.

26. A non-transitory computer-readable storage medium encoded with instructions that, when executed on a processor, perform the method according to claim 25.

* * * * *